(12) United States Patent
Freer et al.

(10) Patent No.: US 10,694,946 B2
(45) Date of Patent: Jun. 30, 2020

(54) DUAL EEG NON-CONTACT MONITOR WITH PERSONAL EEG MONITOR FOR CONCURRENT BRAIN MONITORING AND COMMUNICATION

(71) Applicant: Freer Logic, Inc., Skyland, NC (US)

(72) Inventors: Peter Anthony Freer, Fletcher, NC (US); Gwen Kathryn Freer, Fletcher, NC (US)

(73) Assignee: Freer Logic, Inc., Skyland, NC (US)

( * ) Notice: Subject to any disclaimer, the term of this patent is extended or adjusted under 35 U.S.C. 154(b) by 413 days.

(21) Appl. No.: 15/631,426

(22) Filed: Jun. 23, 2017

(65) Prior Publication Data

US 2018/0008145 A1 Jan. 11, 2018

Related U.S. Application Data

(60) Provisional application No. 62/358,367, filed on Jul. 5, 2016.

(51) Int. Cl.
*A61B 5/00* (2006.01)
*A61B 5/04* (2006.01)
(Continued)

(52) U.S. Cl.
CPC .......... *A61B 5/0006* (2013.01); *A61B 5/0404* (2013.01); *A61B 5/04007* (2013.01);
(Continued)

(58) Field of Classification Search
CPC ........... A61B 5/00; A61B 5/0205; A61B 5/04; A61B 5/0404; A61B 5/0408;
(Continued)

(56) References Cited

U.S. PATENT DOCUMENTS 6,097,981 A 8/2000 Freer
6,402,520 B1 6/2002 Freer
(Continued)

OTHER PUBLICATIONS

International Search Report and Written Opinion dated Sep. 15, 2017 in PCT/US17/40733 filed on Jul. 5, 2017.

*Primary Examiner* — Eric J Messersmith
(74) *Attorney, Agent, or Firm* — Oblon, McClelland, Maier & Neustadt, L.L.P.

(57) ABSTRACT

Aspects of the disclosure can provide a method and device for detecting EEG signals of a first person in proximity to the device. The device can include a non-contact EEG directional circuit having non-contact sensors, the non-contact EEG directional circuit being configured to detect the EEG signals produced by a brain of the first person without making contact with the first person. The device can further include a processor coupled to the non-contact EEG directional circuit that is configured to analyze the EEG signals to detect patterns in the EEG signals that correspond to a state of the first person in proximity to the non-contacting sensor and a feedback device that is configured to provide a second person with an indication of the state of the first person in proximity to the non-contacting sensor. Additionally, the device can include a contact EEG circuit having sensors that are in contact with the second person and that is configured to detect second EEG signals produced by a brain of the second person, wherein the processor is coupled to the contact EEG circuit and is configured to analyze the second EEG signals to detect patterns in the second EEG signals that correspond to a state of second the person.

25 Claims, 14 Drawing Sheets

(51) Int. Cl.
*A61B 5/0404* (2006.01)
*A61B 5/0408* (2006.01)
*A61B 5/0478* (2006.01)
*A61B 5/0482* (2006.01)
*A61B 5/0205* (2006.01)
*A61B 5/048* (2006.01)
*A61B 5/16* (2006.01)

(52) U.S. Cl.
CPC ........ *A61B 5/04008* (2013.01); *A61B 5/0478* (2013.01); *A61B 5/0482* (2013.01); *A61B 5/04085* (2013.01); *A61B 5/681* (2013.01); *A61B 5/0205* (2013.01); *A61B 5/048* (2013.01); *A61B 5/04014* (2013.01); *A61B 5/04017* (2013.01); *A61B 5/165* (2013.01); *A61B 5/168* (2013.01); *A61B 5/7455* (2013.01); *A61B 2562/0209* (2013.01); *A61B 2562/0223* (2013.01); *A61B 2562/04* (2013.01)

(58) Field of Classification Search
CPC ..... A61B 5/0478; A61B 5/048; A61B 5/0482; A61B 5/16; A61B 5/0006; A61B 5/7455; A61B 5/681; A61B 5/168; A61B 5/165; A61B 5/04085; A61B 5/04017; A61B 5/04014; A61B 5/04008; A61B 5/04007; A61B 2562/0223; A61B 2562/0209; A61B 2562/04
See application file for complete search history.

(56) References Cited

U.S. PATENT DOCUMENTS

| | | |
|---|---|---|
| 6,626,676 B2 | 9/2003 | Freer |
| 8,209,004 B2 | 6/2012 | Freer et al. |
| 8,391,967 B2 | 3/2013 | Freer et al. |
| 2004/0230549 A1 | 11/2004 | Freer et al. |
| 2008/0275358 A1 | 11/2008 | Freer et al. |
| 2010/0245091 A1 | 9/2010 | Singh et al. |
| 2011/0043225 A1 | 2/2011 | Sullivan et al. |
| 2012/0232410 A1 | 9/2012 | Freer et al. |
| 2014/0145859 A1 | 5/2014 | Eggenberger et al. |
| 2014/0221866 A1 | 8/2014 | Quy |
| 2015/0087931 A1* | 3/2015 | Banerjee ............ A61B 5/02405 600/301 |
| 2016/0103487 A1 | 4/2016 | Crawford et al. |

* cited by examiner

DUAL EEG NON-CONTACT MONITOR WITH PERSONAL EEG MONITOR FOR CONCURRENT BRAIN MONITORING AND COMMUNICATION

INCORPORATION BY REFERENCE

This present disclosure claims the benefit of U.S. Provisional Application No. 62/358,367, "DUAL EEG NON-CONTACT MONITOR WITH PERSONAL EEG MONITOR FOR CONCURRENT BRAIN MONITORING AND COMMUNICATION" filed on Jul. 5, 2016, which is incorporated herein by reference in its entirety.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

The term electroencephalography (EEG) generally refers to the measurement of electrical activity produced by the brain as measured or recorded from electrodes placed on the scalp of a person. The resultant electrical signals from the electrodes are correspondingly termed EEG signals, and are based on the electrical activity within the brain of a person. Such electrical activity is commonly termed "brainwave" activity. A related term, electroencephalogram, refers to a graphic record produced by an EEG.

A system for naming points on the scalp or head where EEG electrodes are attached has been developed. Thus, the International "10-20" system is widely used to describe the location of EEG scalp electrodes for standardization. The 10-20 system is based on the surface placement of the electrode and its relationship to the underlying area of cerebral cortex. The "10" and "20" refer to the actual distances between adjacent electrodes as either 10% or 20% of the total front-back or right-left distance of the skull. Further, the letters F, T, C, P and O, which stand for Frontal, Temporal, Central, Parietal and Occipital, respectively, are used to identify the lobe over which the sensor is placed. A number is further used to identify the hemisphere location. Even numbers (2, 4, 6, 8) refer to electrode positions on the right hemisphere, and odd numbers (1, 3, 5, 7) refer to electrode positions on the left hemisphere.

When using electrodes that are placed on the scalp or head, possibly in accordance with the International "10-20" system, the transmission of the resulting electrical signals corresponding to brainwave activity over wires is referred to telegraph facilitated human-to-human communication over distance. Electrocorticography or intracranial electroencephalography (iEEG) where electrophysiological monitoring of EEG can be performed by placing electrodes directly on the exposed surface of the brain. This, of course, is highly invasive. Such direct brain-to-brain interfaces (BBI) is a modern extension of the early telegraph technology.

SUMMARY

Aspects of the disclosure can provide a method and device for detecting EEG signals of a first person in proximity to the device. The device can include a non-contact EEG directional circuit having non-contact sensors, the non-contact EEG directional circuit being configured to detect the EEG signals produced by a brain of the first person without making contact with the first person. The device can further include a processor coupled to the non-contact EEG directional circuit that is configured to analyze the EEG signals to detect patterns in the EEG signals that correspond to a state of the first person in proximity to the non-contacting sensor and feedback device that is configured to provide a second person with an indication of the state of the first person in proximity to the non-contacting sensor.

Additionally, a device of the disclosure can include a contact EEG circuit having sensors that are in contact with the second person and that is configured to detect second EEG signals produced by a brain of the second person, wherein the processor is coupled to the contact EEG circuit and is configured to analyze the second EEG signals to detect patterns in the second EEG signals that correspond to a state of second the person.

Additional aspects of the disclosure can provide a device that can further include a transceiver that is configured to transmit the state of second the person to another device and receive a signal corresponding to a state of another person from the other device. The feedback device can provide the second person with the indication of the state of the other person based on the signal received by the transceiver, where the feedback device can be a multi-channel electro stimulator array or an electromagnetic sensor coil.

In other aspects of the disclosure, the state of the first person in proximity to the non-contacting sensor can be an emotional state, a cognitive load state, or an alertness state of the first person. Further, the state of the first person in proximity to the non-contacting sensor can be an attention, stress, thought, peak performance, like/dislike, cognitive states, mental states, or psycho-physiological states.

In the device according to the disclosure, the processor can match the detected patterns in the EEG signals to an EEG signature corresponding to the first person in proximity to the non-contacting sensor in order to identify the first person. Further, the processor can search a database of EEG signatures for an EEG signature corresponding to the detected EEG signals produced by the brain of the first person in order to identify the first person.

Additional aspects of the disclosure disclose a system and method of monitoring electrical activity within the brain of a person for purposes such as, but not limited to, bio feedback-based attention training, monitoring cognitive state, monitoring motions, monitoring drowsiness, monitoring stress monitoring cognitive load, human performance training, gaming, relaxation training, identification, and thought transfer through brain to brain interface (BBI) assisted by a computer. Specifically, aspects of the disclosure can permit communication between two people wearing a device according to the disclosure. For example, a sender brain (person 1) can emit a neural signal, e.g., "Hello" which has been interpreted through algorithmic function. In its most rudimentary form, the word, "Hello," may simply cause a peak at a specific EEG frequency of hertz (Hz). This is an analog signal that can be digitized via an analog to digital (A/D) converter which sends the digitized information to via Bluetooth, WiFi, Internet or the like to a separate person (person 2) wearing a receiver. The receiver device can then use DSP to re-encode the digitized information as a neural message that is then injected into person2's peripheral nervous system by, for example, methods of magnetically (transcranial magnetic stimulation of the visual areas in the occipital cortex indirectly modulating neural activity through rapidly changing magnetic fields), electrically (array of sensors on or under the skin), or haptically stimulating the nerves that induce neural activity that can interpret the signal as, "Hello." These methods can also be used in combination as neurostimulation methods to exchange information between brains directly in neural code.

In one aspect of the disclosure, a method is provided for concurrently monitoring electrical activity within the brains of two persons using a single device, each person having a body including a head. The method can include placing at least one sensor on the skin proximate to portions of the body below the head to develop raw signals of the device wearer, while the same device aimed at, or directed to, the body of a second person without touching the skin of the body of the second person, to develop raw signals through non-contact with the second person and filtering the raw signals to produce analysis signals including frequency components relevant to brain electrical activity of both persons while attenuating unrelated frequency components.

In another aspect of the disclosure, a method is provided for concurrently monitoring electrical activity within the brains of two persons using a single device, each person having a body including a head. The method can include placing at least one sensor on the skin proximate to portions of the body below the head to develop raw signals of the device wearer, while the same device aimed at, or directed to, the body of a second person without touching the skin of the body of the second person, to develop raw signals through non-contact with the second person and processing the raw signals to produce at least one bandpass-filtered state-indicating signal representative of raw signal magnitude within a predetermined frequency range as an indication of the personal identity, physiological, psychophysiological, emotional, or cognitive state of the person.

In yet another aspect, a method is provided for concurrently monitoring electrical activity within the brains of two persons using a single device, each person having a body including a head. The method can include placing at least one sensor on the skin proximate to portions of the body below the head to develop raw signals of the device wearer, while the same device aimed at, or directed to, the body of a second person without touching the skin of the body of the second person to develop raw signals, and analyzing the signals to provide an indication of the person's level of attention by isolating frequency components relevant to brain electrical activity indicative of the person's level of attention while attenuating unrelated frequency components.

In still another aspect, apparatus is provided for concurrently monitoring electrical activity within the brains of two persons using a single device, each person having a body including a head. The method can include placing at least one sensor on the skin proximate to portions of the body below the head to develop raw signals of the device wearer, while the same device aimed at, or directed to, the body of a second person without touching the skin of the body of the second person. The apparatus can include at least one differential sensor, or other sensor type, a unit including at least an amplifier connected for receiving signals from the sensors, a non-body contact directional EEG device configured for aiming the sensors at a portion of the person's body below the head, the non-body contact directional EEG device providing structural support for the sensors and for the unit, and the non-body contact directional EEG device positioning the sensors at least proximate to the body of the person without touching the skin of the body, a body-contact unit, for example, a wrist worn device ('wearable'), and a programmed computing device receiving signals from the amplifier. The unit and the computing device may function together to isolate and analyze frequency components of the signals relevant to brain electrical activity while attenuating unrelated frequency components.

In yet another aspect, a method is disclosed that provides for concurrently monitoring electrical activity within the brains of two persons using a single device, each person having a body including a head. The method can include placing at least one sensor on the skin proximate to portions of the body below the head to develop raw signals of the device wearer, while the same device aimed at, or directed to, the head of a second person without touching the skin of the head of the second person. The method can include directing at least one non-contact sensor at least proximate to portions of the head without touching the skin or hair of the head of the second person to develop raw signals, and filtering the raw signals to produce analysis signals including frequency components relevant to brain electrical activity while attenuating unrelated frequency components.

In another aspect, a method is disclosed for concurrently monitoring electrical activity within the brains of two persons using a single device, each person having a body including a head. The method can include placing at least one sensor on the skin proximate to portions of the body below the head to develop raw signals of the device wearer, while the same device aimed at, or directed to, the head of a second person without touching the skin of the head of the second person. The method can include placing at least one non-contact sensor at least proximate to portions of the head without touching the head to develop raw signals, and processing the raw signals to produce at least one bandpass-filtered state-indicating signal representative of raw signal magnitude within a predetermined frequency range as an indication of the personal identity physiological, psychophysiological, emotional, or cognitive state of the person.

In yet another aspect, the disclosure provides a method for concurrently monitoring electrical activity within the brains of two persons using a singular device, each person having a body including a head. The method can include placing at least one sensor on the skin proximate to portions of the body below the head to develop raw signals of the wearer, while the same device aimed at, or directed to, a second person without touching the skin of the body of the second person, to develop raw signals through non-contact with the second person. The method can include placing at least one sensor at least proximate to portions of the head of a second person without touching the skin or hair of the head to develop signals, and analyzing the signals to provide an indication of the person's level of attention by isolating frequency components relevant to brain electrical activity indicative of the person's level of attention while attenuating unrelated frequency components.

In still another aspect, the disclosure can provide an apparatus for concurrently monitoring electrical activity within the brains of two persons using a singular device, each person having a body including a head. The method can include placing at least one sensor on the skin proximate to portions of the body below the head to develop raw signals of the wearer, while the same device aimed at, or directed to, a second person without touching the skin of the body of the second person, to also simultaneously develop raw signals through non-contact with the second person. The apparatus can include, but not be limited to, at least one differential or other sensor type, a unit including at least an amplifier connected for receiving signal from the sensors, a non-body contact directional EEG device configured for aiming the sensors at a portion of the person's head, the non-body contact directional EEG device providing structural support for the sensors and for the unit, the non-body contact directional EEG device positioning the sensors at least proximate to the head of the person without touching the skin of the head, at least one differential or other sensor type connected to the body of the device wearer; and a programmed computing device receiving signals from the amplifier to alter such signals by algorithm and digital signal processing to send to a connected multi-channel electromagnetic sensor array, electromagnetic coil or other transmission device. The united the computing device may function together to isolate and analyze frequency components of the signals relevant to brain electrical activity while attenuating unrelated frequency components, after those signals to thought based signals to then transmit thought in the form of brain electrical activity between two persons allowing one person to transmit thoughts to the other through a single or multi-channel electro-magnetic sensor array or electro-magnetic coil other transmission device attached to the peripheral nervous system, for example, a person's external body or epidermis.

BRIEF DESCRIPTION OF THE DRAWINGS

Various embodiments of this disclosure that are proposed as examples will be described in detail with reference to the following figures, wherein like numerals reference like elements, and wherein.

DETAILED DESCRIPTION OF EMBODIMENTS

Figure 1:
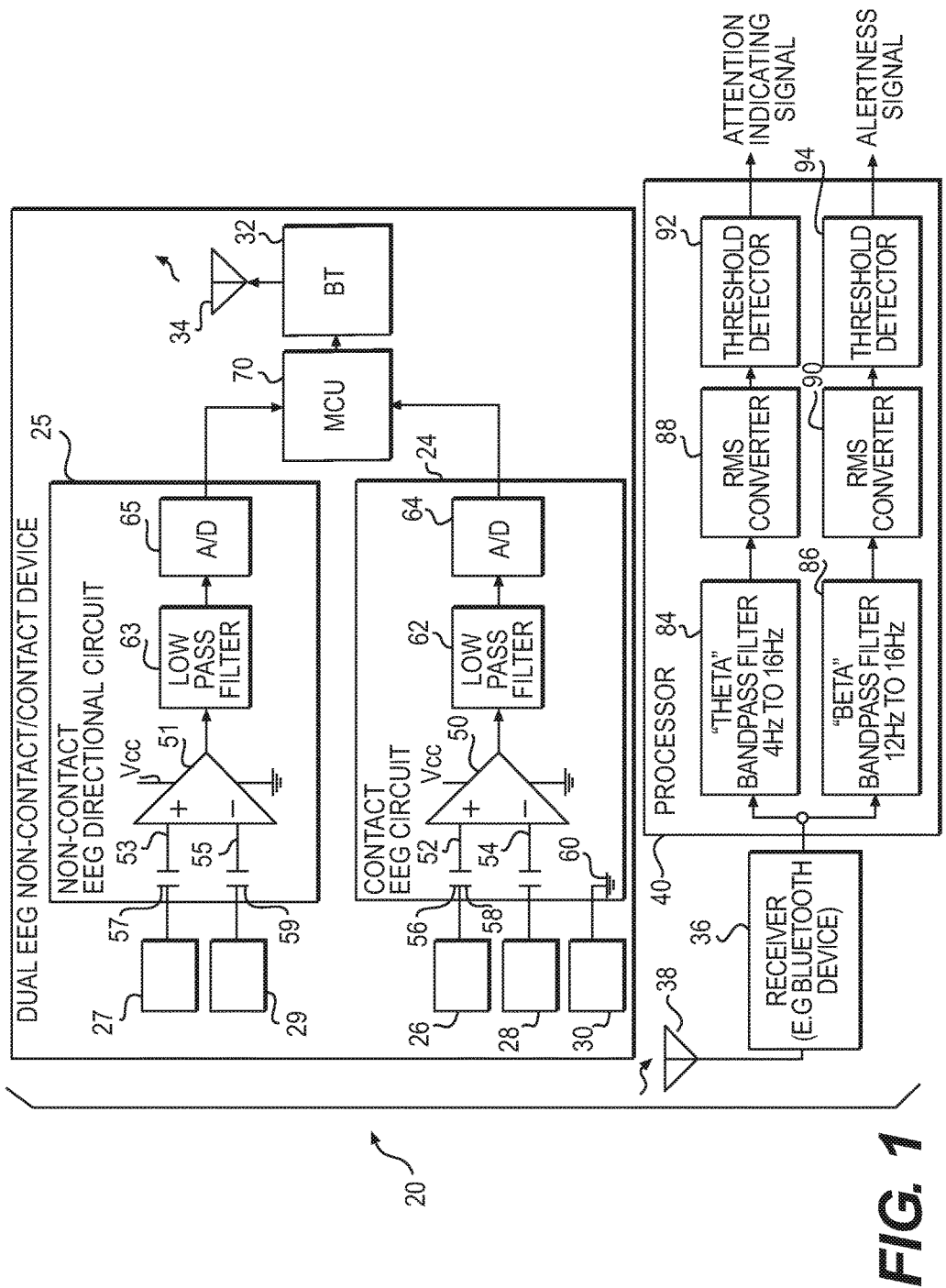
FIG. 1 is a schematic representation of an exemplary apparatus embodying the disclosure.

Aspects of the disclosure can provide a personal wearable apparatus and methods for monitoring brainwaves that employ electrode attachment to the head or body of a first person while simultaneously using non-contact EEG emanating from the same device using a separate set of differential electrodes, or other types, directed to portions of the head or body below the head from a distance without touching either the skin, clothing, or hair of the head or body of a second person to monitor brain signals of the second person. This unique pairing can provide a distinct advantage over the use of separate systems simultaneously. For example the disclosure can provide a discreet monitoring of another person's EEG data and using those data to algorithmically produce personal identity, physiological, psycho-physiological, emotional, or cognitive states of the person being monitored. As an example, the device could be used discreetly on a date involving two people. By placing the wrist worn wearable device worn by a first person in proximity to a second person, and by activating the non-contact EEG, the first person wearing the device can discretely obtain an EEG reading from the second person. By analyzing the EEG signal from the second person, one could obtain the interest level of the second person, for example, whether the second person found the first person likeable, was stressed, was paying attention, was excited, and the like. These data could be reported to the wearer discreetly through the device and/or on their cell phone screen which may change color based on the other person's cognitive or psycho-physiological state. Additionally, the data may be displayed on the cell phone screen through a graphic descriptive of the other person's mental state. Finally, the wearable device could emit auditory, visual, or haptic responses to the wearer indicating the aforementioned data. It is possible with the addition of a video screen to the wearable device, that the device may report all data in its various embodiments.

Such a personal wearable device discretely can detect another person's EEG who is in proximity. Another embodiment could be used by a security agency to obtain the mental or cognitive state of an individual, for example traveling at an airport, because it does not require direct contact or require very close proximity to the head. The device can incorporate both the non-contact EEG (no physical connection to the head or body of the person while being able to monitor EEG signals emanating from the person's brain using common differential sensor materials such as, but not limited to stainless steel, conductive plastics, or other common conductive materials.

The unique combination of two devices, a body-based EEG acquisition and non-contact EEG acquisition embedded in a single wearable device, creates a totally new paradigm of use, namely wirelessly transferring thought between two separate persons, also known as 'mind reader' technology. EEG technology as embodied in this disclosure can provide the basis for thought transfer over distances using simple personal wearable devices by transmitting EEG waveforms, using digital signal processing and algorithmic transformations of the EEG data, and other data including, but not limited to heart rate, via wireless technology such as, but limited to, Bluetooth, WiFi, infrared, Internet, and other wired and wireless technologies, decoding this information as thought to an electro stimulator, and passing the thought to the brain of a wearer of the device through, but not limited to, a single or multi-channel electro-magnetic sensor array or electro-magnetic coil connected to the peripheral nervous system. This can be the foundation for thought transfer or 'mind reader' technology that allows thoughts to be shared without vocalization or physical connection to another human being.

The non-contact aspect of the apparatus may be used at a distance, such six inches or more, from the body and obtain EEG signal through material, such as hair or clothing, thus making it practical to use. It does not require signal injection into a subject to obtain EEG data. However, aspects of the disclosure may require signal injection into the body of the wearer to transmit thoughts of a second person to the brain of the person wearing the device. This may be embodied as a digital-to-analog (D/A) converter, analog low pass filter, and power amplifier which are controlled by an array controller which is connected to an array of multiple electrodes or magnetic coil before being transmitted to the peripheral nervous system and brain of the human wearing the body-contact EEG amplifier and wireless transmission unit using via single or multi-channel electromagnetic sensor array or electromagnetic coil connected to the peripheral nervous system of the body. Additionally, the device may also be embodied as two non-contact personal devices.

Studies of the brain have found that EEG signals include a number of components, including signals resulting from rhythmic activity that fall within a number of frequency bands. Generally accepted terminology for signals within these various frequency bands includes delta (up to 3 Hz), theta (4 Hz to 8 Hz), alpha (8 Hz to 12 Hz), beta (12 Hz to about 30 Hz), and gamma (approximately 26 Hz to 100 Hz). Although these different brainwave signals are produced simultaneously and in combination, the frequency band within which signals are dominant (strongest) at any point in time is an indication of the state of consciousness of a person, or of the physiological state of the person.

As examples, during sleep, the brain produces dominants low delta waves with a frequency range up to 3 Hz. These tend to be the highest in amplitude and are the slowest waves. Theta waves in the frequency range from 4 Hz to 8 Hz are commonly associated with daydreaming or being in the twilight of sleep or drowsiness. Alpha waves in the frequency range from 8 Hz to 12 Hz are indicative of relaxation. Beta waves in the frequency range from 12 Hz to about 30 Hz are associated with active thinking or alertness. Gamma waves in the frequency range approximately 26 Hz to 100 Hz are theorized to represent cohesiveness of different populations of neurons working together to form a network for the purpose of carrying out a certain cognitive or motor function. Because of filtering properties of the skull and scalp, gamma waves can are generally recorded by using electrodes placed directly on the exposed surface of the brain through an invasive procedure known as electrocorticography (ECoG) which requires a craniotomy.

Signal acquisition for monitoring electrical activity within the brain has been conventionally limited to the use of electrodes attached to the human head, and typically to the scalp, for a variety of reasons. Electrode placement on the head can be limiting for a variety of reasons. As one example, if a person is active in a sport or movement, electrical activity within the brain cannot be accurately monitored using head-bound EEG electrodes because the movement of the head during the activity interferes with the signal acquisition itself by creating artifacts. Moving electrodes can disrupt signal input/output. Also, if a person has a head injury or traumatic brain injury (TBI), that person may not be able to withstand sensors placed on the head due to tissue damage. For use in a vehicle, attachment of electrodes to the head has been rejected by the public. Contact or even close proximity to the skin of the head incorporated in traditional wired EEG acquisition sensors and modern consumer headsets have made EEG use somewhat prohibitive in the consumer marketplace. For example, they can reinforce a negative science fiction stereotype that connotes an intimidating or frightening effect attributable to visible wires attached to the head.

The apparatus disclosed herein can particularly useful in the fields of monitoring EEG-based neurofeedback, detecting attention, detecting personal identity, detecting cognitive states, detecting human emotions, detecting cognitive load, detecting drowsiness and sleep, and the like. However, such are by way of example only, and not limitations. Accordingly, embodiments of the disclosure may be employed to acquire and analyze signals based on electrical activity within the brain of a person for a wide variety of purposes.

FIG. 1 shows an exemplary apparatus 20 that can include both a non-contact EEG directional circuit 25 and a contact EEG circuit 24. The non-contact EEG directional circuit 25 can be configured for placement near a person's body near or below the head to detect brain activity without making contact with the person. Various exemplary embodiments thereof are described in detail below with reference to FIGS. 4-12. In operation, the non-contacting sensors 27 and 29 and the non-contact EEG directional circuit 25 can be placed at least proximate to and directed to portions anywhere on the body or head of a person positioned and separate from the person having the apparatus 20. The sensors 27 and 29 develop raw signals including frequency components relevant to brain electrical activity ("brainwave" signals) of the person. The contact EEG circuit's 24 sensors 26 and 28 can be placed in contact proximate a body of a person below the head to develop raw signals including frequency components relevant to brain electrical activity ("brainwave" signals).

In an embodiments wireless transmitter 32 and an associated antenna 34 can be shared between the non-contact EEG directional circuit 25 and contact EEG circuit 24. The apparatus 20 additionally may include a corresponding wireless receiver 36 and an associated antenna 38. The wireless receiver 36 can transmit signals received from either the non-contact EEG directional circuit 25 or contact EEG circuit 24 to a processor 40, such as a personal compute (PC). The processor 40 can be configured to control the components of the apparatus to process the detected EEG data and wirelessly transmit the EEG data to other devices, as necessary. Among other functions, the processor 40 can perform signal processing and analysis based on raw brainwave signals developed by the sensors 26, 27, 28, and 29.

The exemplary apparatus 20 can be controlled through the microcontroller unit (MCU) 70 to control and transmit signals of EEG data from the non-contact EEG directional circuit 25 and contact EEG circuit 24 individually or simultaneously. Of course, it should be understood that the functions performed by the processor 40 can be distributed so as to be partially or entirely performed by the apparatus 20 for example, in by the MCU 70.

In the exemplary configuration illustrated in FIG. 1, the body-contact EEG circuit 24 includes an amplifier 50 having a pair of high impedance inputs 52 and 54 to which the active electrodes 26 and 28 are connected through AC coupling capacitors 56 and 58. Shielded leads (not specifically shown) may be employed. Even so, advantageously, the electrodes 26 and 28 can be located near the amplifier 50, minimizing the required lead length. A ground electrode 30, if employed, is connected to circuit ground 60. Additionally, the non-contact EEG directional circuit 25 includes an amplifier 51 having a pair of high-impedance inputs 53 and 55 to which the active non-contact electrodes 27 and 29 are connected through AC coupling capacitors 57 and 59. Shielded leads (not specifically shown) may be employed. Even so, advantageously, the electrodes 27 and 29 can located near the amplifier 51, minimizing the required lead length. Depending on the design and use of the device, a ground may not be necessary.

The body-contact EEG circuit 24, in addition to the amplifier 50, can include a low-pass filter 62 and an analog-to-digital converter (A/D) 64 connected to the wireless transmitter 32. The low pass filter 62 serves to attenuate or minimize signal frequency components which are above a frequency band of interest and which are unrelated to electrical activity within the brain of a person. A potential frequency component unrelated to and not relevant to brain electrical activity is a signal coupled from 50 Hz or 60 Hz AC power lines. A low pass filter 62 having a cut-off frequency within the range 20 to 40 Hz is suitable. As a more particular example, the low pass filter 62 can be a fifth order switched capacitor low pass filter having a cut off frequency of 22 Hz. In the FIG. 1 embodiment, brainwave signal components of interest are well below 50 Hz or 60 Hz, and the 22 Hz low pass filter 62 is simple and effective. In applications in which frequency ranges of brainwave signal components of interest include 50 Hz or 60 Hz, a notch filter may be employed instead of the low pass filter 62. Further details of the structure and operation of the body-contact EEG circuit 24 are described in U.S. Pat. No. 8,209,004 entitled "BODY-BASED MONITORING OF BRAIN ELECTRICAL ACTIVITY" that issued on Jun. 26, 2012 and U.S. Pat. No. 8,391,967 entitled "BODY-BASED MONITORING OF BRAIN ELECTRICAL ACTIVITY" that issued on Mar. 5, 2013, both of which are hereby incorporated herein by reference in their entirety.

Similarly, in the non-contact EEG directional circuit 25, in addition to the amplifier 51, the circuit can include a low pass filter 63 and an analog-to-digital converter (A/D) 65 connected to the shared wireless transmitter 32. The low pass filter 63 serves to attenuate or minimize signal frequency components which are above a frequency band of interest and which are unrelated to electrical activity within the brain of a person. A potential frequency component unrelated to and not relevant to brain electrical activity is a signal coupled from 50 Hz or 60 Hz AC power lines. A low pass filter 63 having a cut off frequency within the range 20 to 40 Hz is suitable. As a more particular example, the low pass filter 63 is a fifth order switched capacitor low pass filter having a cut off frequency of 22 Hz. In the FIG. 1 embodiment, brainwave signal components of interest are well below 50 Hz or 60 Hz, and the 22 Hz low pass filter 63 is simple and effective. In applications in which frequency ranges of brainwave signal components of interest include 50 Hz or 60 Hz, a notch filter may be employed instead of the low pass filter 63. Further details of the structure and operation of the non-contact EEG directional circuit 25 are described in U.S. patent application Ser. No. 15/497,734, entitled "NON-CONTACT BODY AND HEAD-BASED MONITORING OF BRAIN ELECTRICAL ACTIVITY" that was filed on Apr. 26, 2017, which is hereby incorporated herein by reference in its entirety.

The analog to digital (A/D) converters 64 and 65 in both the body-contact amplifier and wireless transmission unit and non-contact amplifier and wireless transmitter unit respectively, can be a 12 bit A/D converter that has a sample rate of 150 Hz. A shared wireless transmitter 32 can included as part of and is representative of a Bluetooth® device 32 incorporating a microchip radio transceiver. Although the wireless transmitter 32 is thus a radio (RF) transmitter 32, of course other forms of wireless communication may as well be employed, such as infrared (IR). A suitably programmed shared microcontroller 70 also is included within the apparatus 20. The microcontroller 70 in a conventional manner can be connected to and at least in part serves the functions of the low pass filters 62 and 63, the A/D converter 64 and 65 as well as the Bluetooth® device 66 (connections not shown). Further, the microcontroller can be configured to control the components of the circuits 24 and 25 to process EEG data and wirelessly communicate data with other devices, as necessary. Additionally, under the control of the microcontroller 70, data can be transmitted and received between other devices for further processing and/or control of other devices.

The various elements within apparatus 20 including both the non-contact EEG directional circuit 25 and contact EEG circuit 24 may be implemented by employing a combination of digital and analog technologies. Moreover, both the non-contact EEG directional circuit 25 and contact EEG circuit 24 may be implemented as "intelligent" and reprogrammable devices, with the microcontroller 70 executing software to perform various functions. The Bluetooth® device 32 is capable of bidirectional data communications, facilitating modification and adjustments of the functioning of both the body-contact amplifier and wireless transmitter unit 24 and non-contact EEG directional amplifier and wireless transmission unit 25, such as updating "firmware."

Correspondingly, the wireless receiver 36 is included as part of and can be Bluetooth® device 36 which cooperates with the Bluetooth® device 32 to form a bidirectional wireless digital communications link. The device 36 likewise incorporates a microchip radio transceiver. In a representative embodiment, the devices 32 and 36 are configured to emulate a 9600 baud serial port through which 12 bit serial data is transmitted. The serial data can be transmitted as ASCII text, using base 64 encoding. Functionally, from a signal processing point of view, the periodically sampled output of the A/D converter 64 is connected to the programmed digital computer 40. However, as a physical and practical matter, the combination of the body attachment device and the bidirectional wireless communications link effected by the Bluetooth® devices 32 and 36 permits freedom of movement.

Implemented in software within the processor 40, employing digital signal processing (DSP) techniques, can be a pair of bandpass filters, in particular, a "theta" bandpass filter 84 and a "beta" bandpass filter 86. The bandpass filters 84 and 86 are followed by respective RMS converters 88 and 90. Accordingly, brainwave signals are bandpass filtered and processed to determine signal magnitude within the "theta" frequency range 4 Hz to 8 Hz and within the "beta" frequency range 12 Hz to 16 Hz. In the illustrated embodiment used as an example, the output of each of the RMS converters 88 and 90 can be a 10 bit binary number within the range (decimal) 0 to 1023.

As a nonlimiting representation of further signal processing, a pair of threshold detectors 92 and 94 can follow the RMS converters 88 and 90, respectively, to produce attention indicating and alertness signals. Theta waves (4 Hz to 8 Hz) are particularly useful for this particular function (attention indication). A decrease in the magnitude of theta waves is indicative of less daydreaming and an increasing level of attention. In addition, an increase in the magnitude of beta waves (12 Hz to 16 Hz) indicates increasing alertness. In applications where it is desired to determine whether a person is in an attentional state, a decrease in theta wave (4 Hz to 8 Hz) activity in combination with (e.g. in ratio to) beta wave (12 Hz to 16 Hz) activity can be employed as an indicator of attention. A variety of other signal processing and analysis strategies, including analysis of delta, theta, alpha and beta wave activity, can be employed to indicate various physiological states in general of a person, including but not limited to level of attention.

It will be appreciated that the functions represented in FIG. 1 can be distributed in various ways, for example, allocated between both the non-contact EEG directional circuit 25 and contact EEG circuit 24 and the processor 40. Various functions can be performed by both or either the non-contact EEG directional circuit 25 and contact EEG circuit 24. The digital communications link effected by the Bluetooth® devices 32 and 36 can be at different locations within the overall signal processing and analysis paths. Moreover, it should be understood that in the various exemplary embodiments, any of the signal detection, processing analysis functions, haptic, auditory, and/or visual functions can be performed in all or in part within a body attached unit or in a separate device, such as a cell phone or the like.

Figure 2:
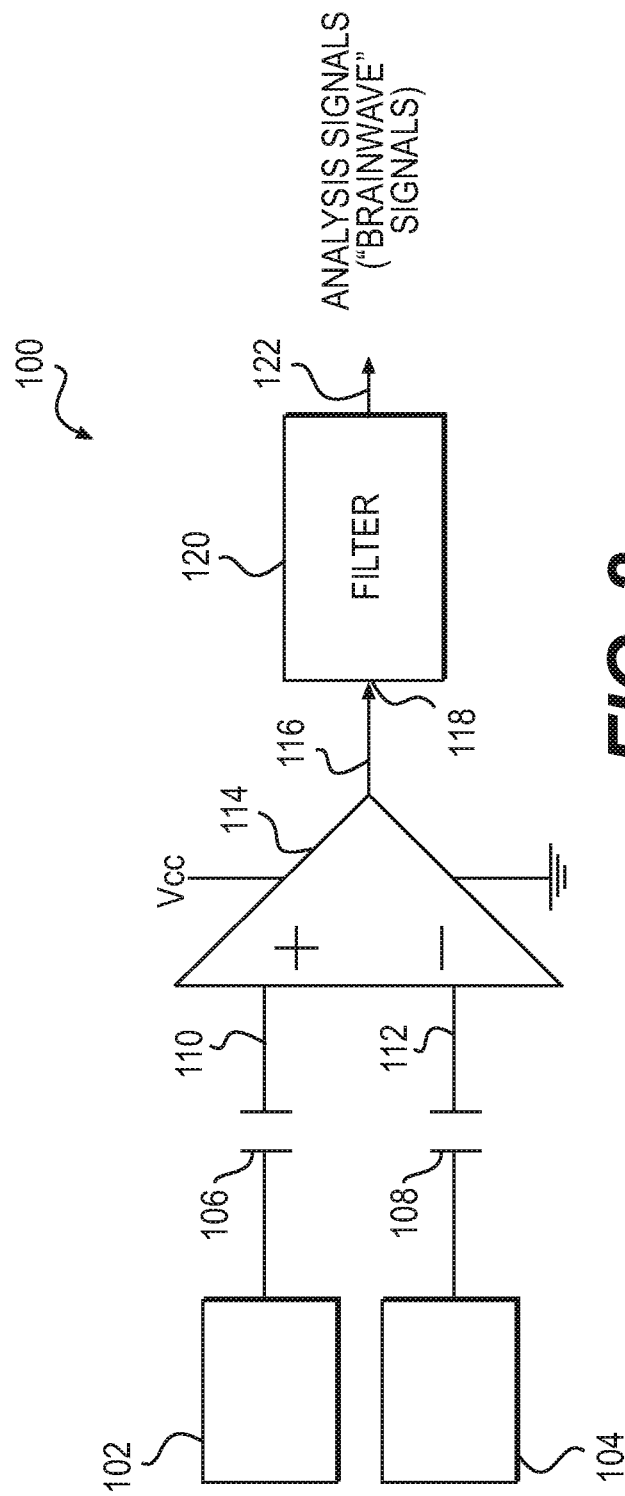
FIG. 2 is an exemplary schematic representation of another apparatus embodying the disclosure.

FIG. 2 shows an exemplary embodiment of a generalized non-contact EEG directional apparatus 100 which produces analysis signals including frequency components relevant to brain electrical activity. In FIG. 2, apparatus 100 can include two representative non-contact sensors 102 and 104, such as active electrodes, that can be coupled through capacitors 106 and 108 to high impedance inputs 110 and 112 of an amplifier 114. The non-contact sensors 102 and 104 can be positioned proximate to portions of a person's body to detect raw brainwave signals. The amplifier 114 has an output 116 connected to an input 118 of a filter 120 that outputs and analysis or brainwave signal. The signal processing in FIG. 2 can be analog, digital, or any combination thereof.

The filter 120 attenuates frequency components which are unrelated to frequency components of interest and which are not relevant to brain electrical activity. Produced at an output 122 of the filter 120 are what may be termed analysis signals corresponding to brainwave signals for further processing and analysis, the analysis signals including frequency components relevant to brain electrical activity. As described above with reference to the filter 62 of FIG. 1, the FIG. 2 filter 120 can be a low pass filter or a notch filter, as examples. The selection and design of the filter 120 depend on the frequency components of interest relevant to brain electrical activity, as well as on particular unrelated frequency components which are anticipated. The filter 120 may be implemented employing digital signal processing (DSP) techniques, and may be adaptive.

The "brainwave" signals at the output 122 of the low pass filter 120 may be employed for a variety of purposes. As described hereinabove, the signals at the output 122 are analysis signals which include frequency components relevant to brain electrical activity, with unrelated frequency components attenuated. The non-contact sensors 102 and 104 can be positioned at least proximate to portions of the body of a person below the head to develop raw signals.

When frequency components relevant to brain electrical activity in general are of interest, particularly when frequency components including delta waves (up to 3 Hz) are of interest, signal components corresponding to a person's heartbeat (approximately 1 Hz to 2 Hz) are unrelated frequency components of particular concern. Unrelated frequency components corresponding to electrical activity of a person's heart are particularly high in magnitude when sensors are connected to portions of the body below the head. The apparatus described herein may be embodied in systems in which signal components in the raw signals resulting from electrical activity of a person's heart are actively attenuated. In an ideal case, signal components resulting from electrical activity of a person's heart are entirely cancelled by active cancellation.

Figure 3:
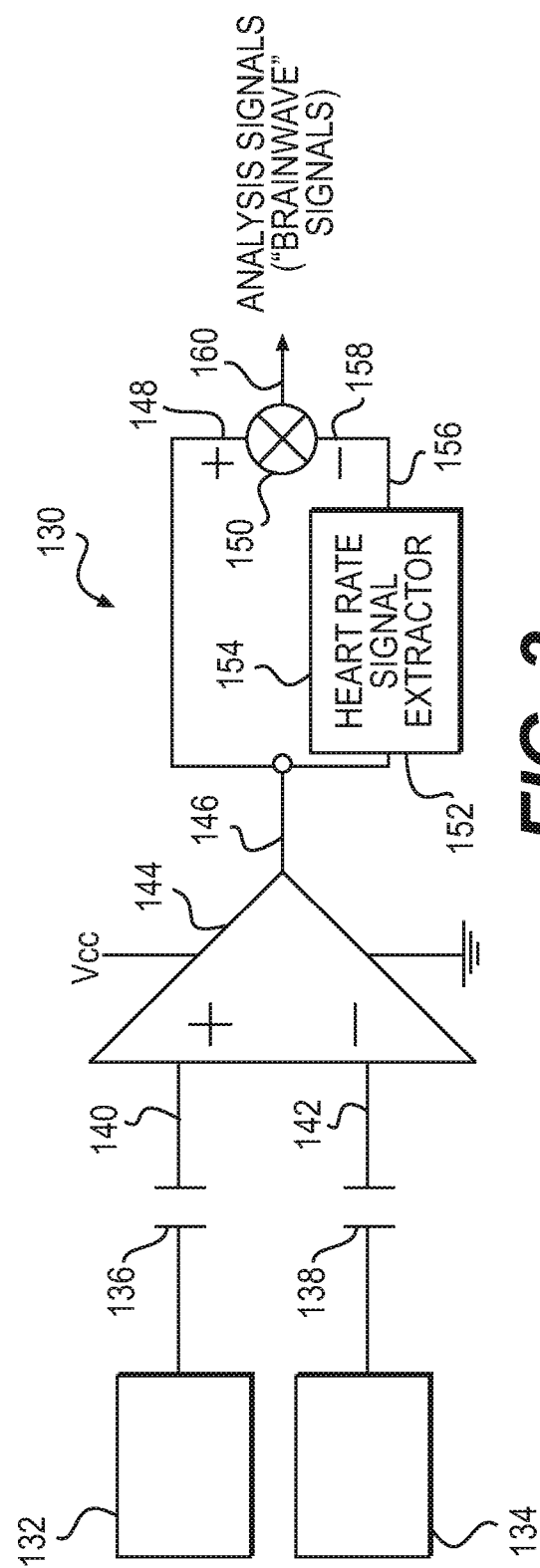
FIG. 3 is an exemplary schematic representation of yet another apparatus embodying the disclosure.

FIG. 3 is a representation of a generalized apparatus 130 which employs such active attenuation to produce analysis signals including frequency-components relevant to brain electrical activity. The FIG. 3 apparatus 130 again employs two representative non-contact sensors 132 and 134 connected through capacitors 136 and 138 to high impedance inputs 140 and 142 of an amplifier 144. At least the non-contact sensors 132 and 134 are positioned proximate to portions of the body of a person below the head to develop raw signals.

The FIG. 3 amplifier 144 has an output 146 connected to two signal branches. One branch is connected to a (+) input 148 of a summing junction 150, and the other to an input 152 of a heart rate signal extractor 154 which extracts signal components resulting from electrical activity of a person's heart. An output 156 of the heart rate signal extractor 154 is connected to a (−) input 158 of the summing junction 150. Analysis signals which include frequency components relevant to brain electrical activity with unrelated frequency components attenuated are produced at the output 160 of the summing junction 150.

Thus, within the summing junction 150, signal components resulting from electrical activity of a person's heart are actively attenuated. Again, in an ideal case, signal components resulting from electrical activity of a person's heart are entirely cancelled by active cancellation.

The heart rate signal extractor 154 can employ digital signal processing (DSP) techniques to recognize, isolate and track signal components resulting from electrical activity of a person's heart. Heart rate monitors can recognize and track a person's heartbeat or heart rate, typically presenting a digital display. The thus recognized, isolated and tracked signal is provided as an output of the heart rate signal extractor 154. With appropriate magnitude adjustment the frequency or signal components resulting from electrical activity of a person's heart can be attenuated or cancelled. Accordingly, the brainwave signal that does not include the electrical activity of a person's heart can be produced at the output 160 of the summing junction 150.

Again, the brainwave signal sat the output 160 of the summing junction 150 may be employed for a variety of purposes. The signals at the output 160 are analysis signals, which include frequency components relevant to brain electrical activity, with unrelated frequency components attenuated. Again, what is significant is that at least the sensors 132 and 134 are positioned proximate to portions of the body of a person below the head to develop raw signals.

As an alternative to the heart rate signal extractor 154 and summing junction of FIG. 3, the topology of FIG. 2 may be employed to provide similar functionality. More particularly, the FIG. 2 filter 120 may be an adaptive DSP filter programmed to attenuate signal components resulting from electrical activity of a person's heart, as well as other signals (such as coupled 50 Hz or 60 Hz AC power line signals) unrelated and not relevant to brain electrical activity.

Signal components resulting from electrical activity of a person's heart can be used for at least two other purposes in embodiments of this disclosure. One such other purpose is to ensure that a body directional device and, in particular, non-contact sensors 26 and 28, 102 and 104, or 132 and 134 are in fact directed at, but not in contact with, or otherwise functionally proximate the body of a person, for convenience collectively referred to as "presence." Ensuring such presence can be employed to ensure that sensed signal components within a brainwave frequency band are in fact representative of brainwaves and are not the result of stray signals coupled from environmental sources, in other words to validate that an EEG signal is being collected. Ensuring such presence can also be employed to conserve battery life, by entering a low power "standby" mode when the absence of signal components resulting from electrical activity of a person's heart indicates no presence.

Another such other purpose is to combine indications resulting from brain electrical activity (i.e., EEG) and from electrical activity of a person's heart (i.e., EKG) for a more comprehensive analysis and indication of a person's cognitive and physiological state. Embodiments of this disclosure thus provide the foundation for a dual technology approach (EEG and EKG) for more comprehensive physiological state monitoring.

Figure 4:
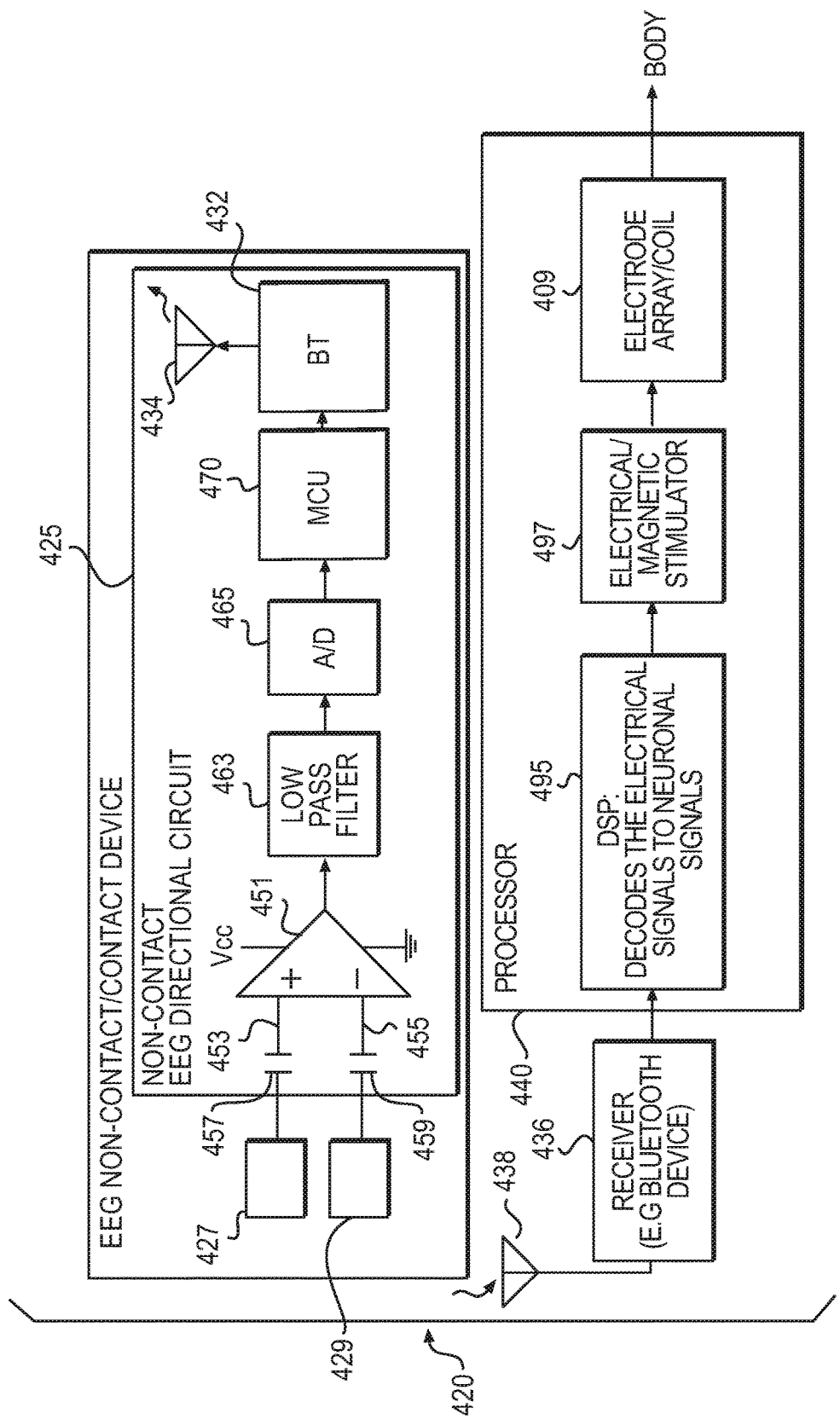
FIG. 4 is an exemplary schematic representation of yet another apparatus embodying the disclosure.

FIG. 4 shows an exemplary embodiment of an apparatus 420 including a non-contact EEG directional circuit 425 which produces analysis signals including frequency components relevant to brain electrical activity. The FIG. 4 non-contact EEG directional circuit 425 can include an amplifier 451 having a pair of high-impedance inputs 453 and 455 to which the active electrodes 427 and 429 are connected through AC-coupling capacitors 457 and 459 to actively acquire EEG of a person in proximity without physical attachment or contact to that person.

The device transmits its EEG data to the receiver 436 which can transmit its data to the processor 440. The data acquired from the other person can be sent to a digital signal processor (DSP) 495 which can be a specialized microprocessor (or a SIB Block), with its architecture optimized for the operational needs of digital signal processing. The DSP 495 can measure, filter, and/or compress continuous real-time EEG signals, and through algorithmic design decode them to neuronal signals. In a practical sense, this decodes the EEG signals acquired from the non-contact EEG directional circuit 425 to neuronal signals that can be transmitted to the brain of the human wearing the body-contact EEG amplifier and wireless transmission unit 424 through the electromagnetic stimulator 497 composed of a digital to analog (D/A) converter, analog low pass filter, and power amplifier connected to an array of single channel or multi-channel electrode sensors or coils 409 through connection to the body's peripheral nervous system.

Figure 5:
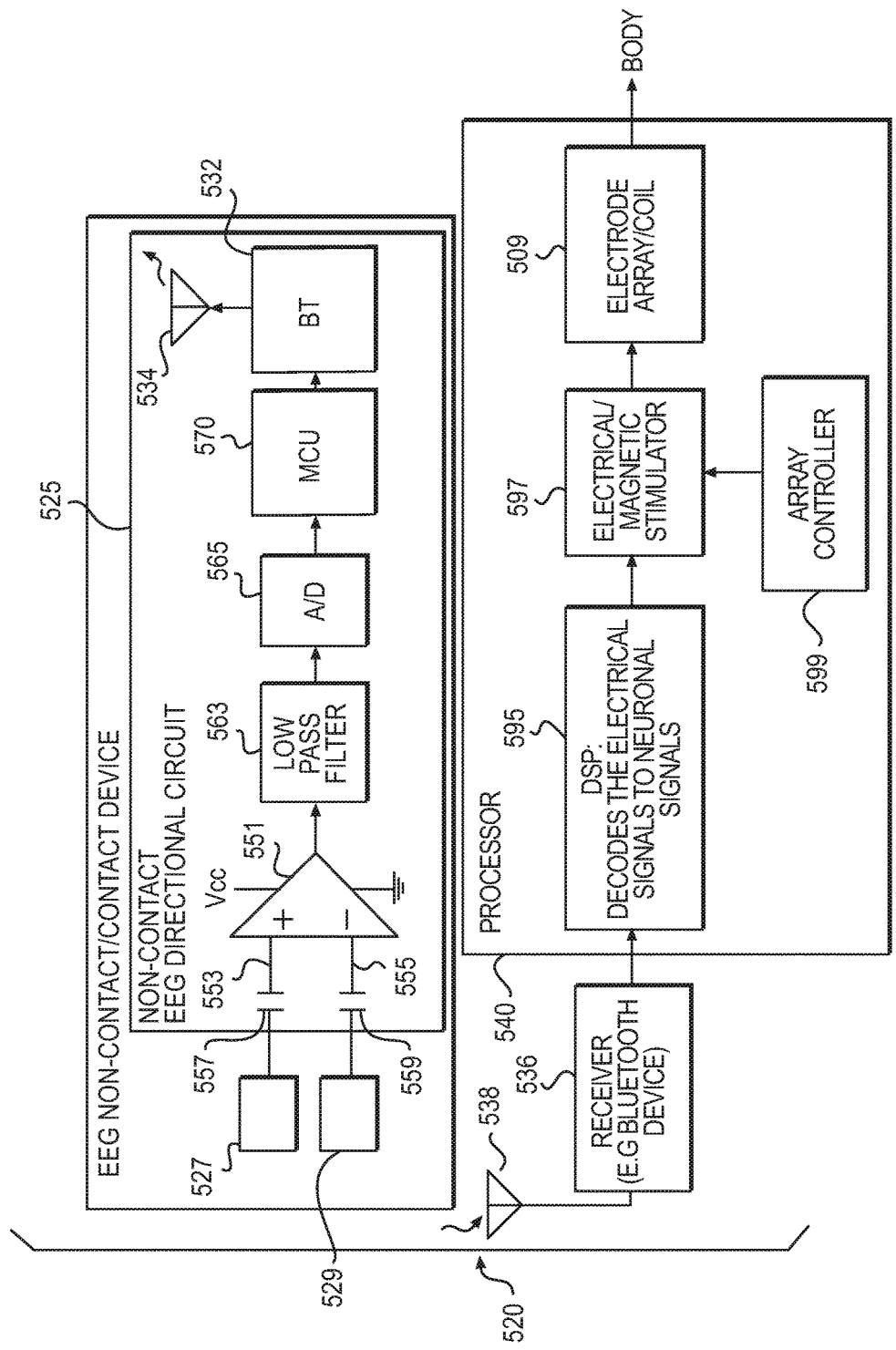
FIG. 5 is a schematic representation of yet another apparatus embodying the disclosure.

FIG. 5 shows an exemplary embodiment of an apparatus 520 having a non-contact EEG directional circuit 525 which produces analysis signals including frequency components relevant to brain electrical activity. The FIG. 5 apparatus can again include an amplifier 551 having a pair of high-impedance inputs 553 and 555 to which the active electrodes 527 and 529 are connected through AC-coupling capacitors 557 and 559 to actively acquire EEG of a person in proximity without physical attachment to that person. The device can transmit EEG data to a Bluetooth receiver 536 which can transmit data to the programmed digital computer 540. The data acquired from the other person are sent to a digital signal processor (DSP) 595 which decodes them to neuronal signals. However, in this embodiment, decoded EEG signals can be transmitted to the electromagnetic stimulator 597 composed of a digital to analog (D/A) converter, analog low pass filter, and power amplifier which can be connected to an array controller 599. The array controller 599 can be connected to an array of multiple electrodes or magnetic coil 509 before being transmitted to the peripheral nervous system and brain of the person wearing the device.

Figure 6:
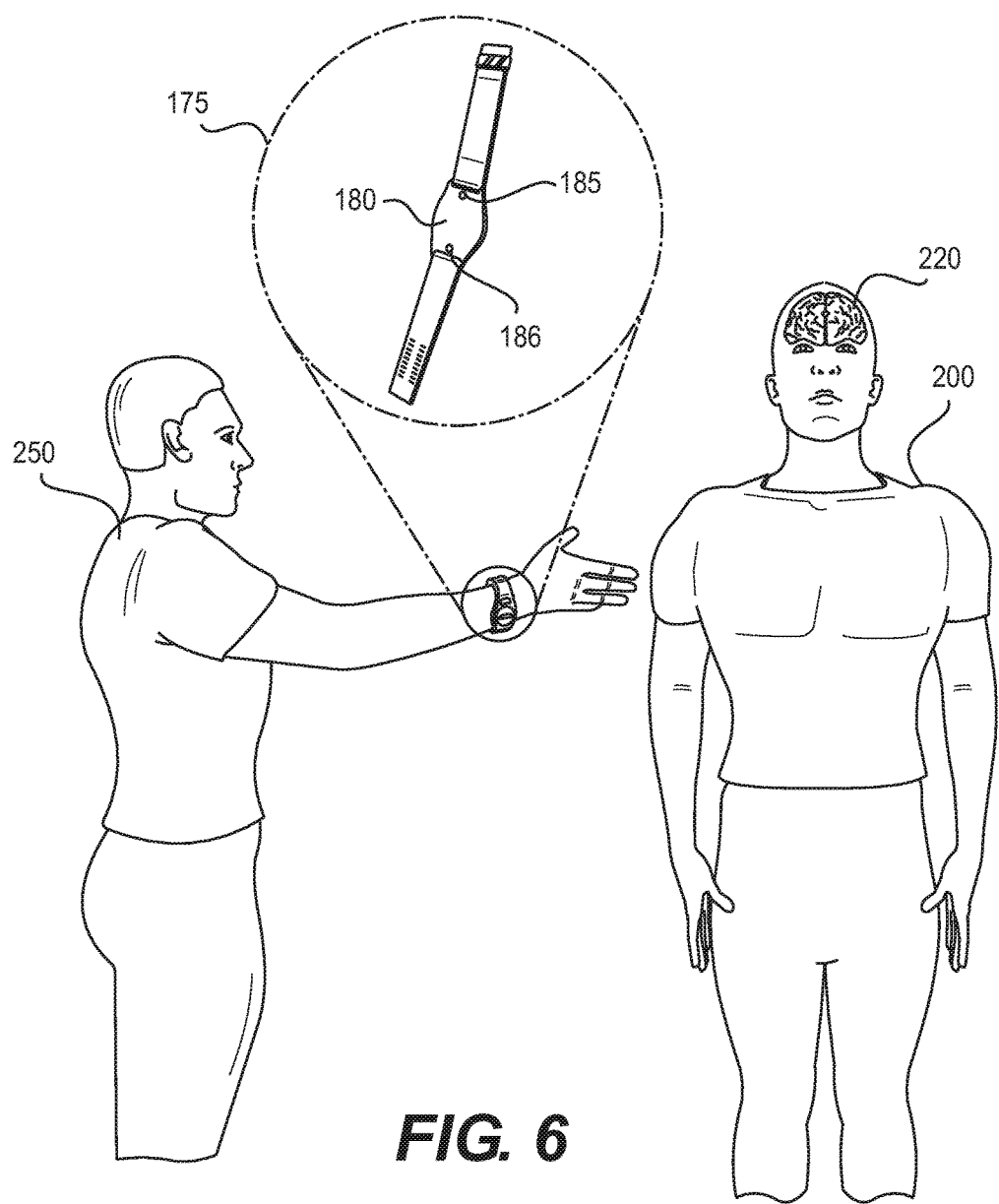
FIG. 6 illustrates an exemplary body-based amplifier with wireless transmitter unit and a non-body contact directional EEG device embedded in a single device, the non-body contact directional EEG device directed to the body of a second person to receive EEG signals from the body of a second person.

FIG. 6 illustrates an exemplary embodiment of a non-body contact/contact directional EEG device 175 shown, for example, as a wristband being worn by a first person 250 and being directed toward the body of a second person 200. The non-body contact directional EEG device 175 of FIG. 6 is configured for directional aiming to a portion of the body of the second person 200 to acquire EEG from the brain 220 of the second person 200 in proximity without physical contact with that second person 200. The non-body contact directional EEG device 175 provides structural support for the internal amplifier and wireless transmitter units 180, and an take the form of, but is not limited to, a wristband housing 175 with external sensor array 185 and 186 as described above with reference to sensors 27 and 29 of FIG. 1 and can be configured for directional aiming of the device to the body of the second person 200.

Figure 7:
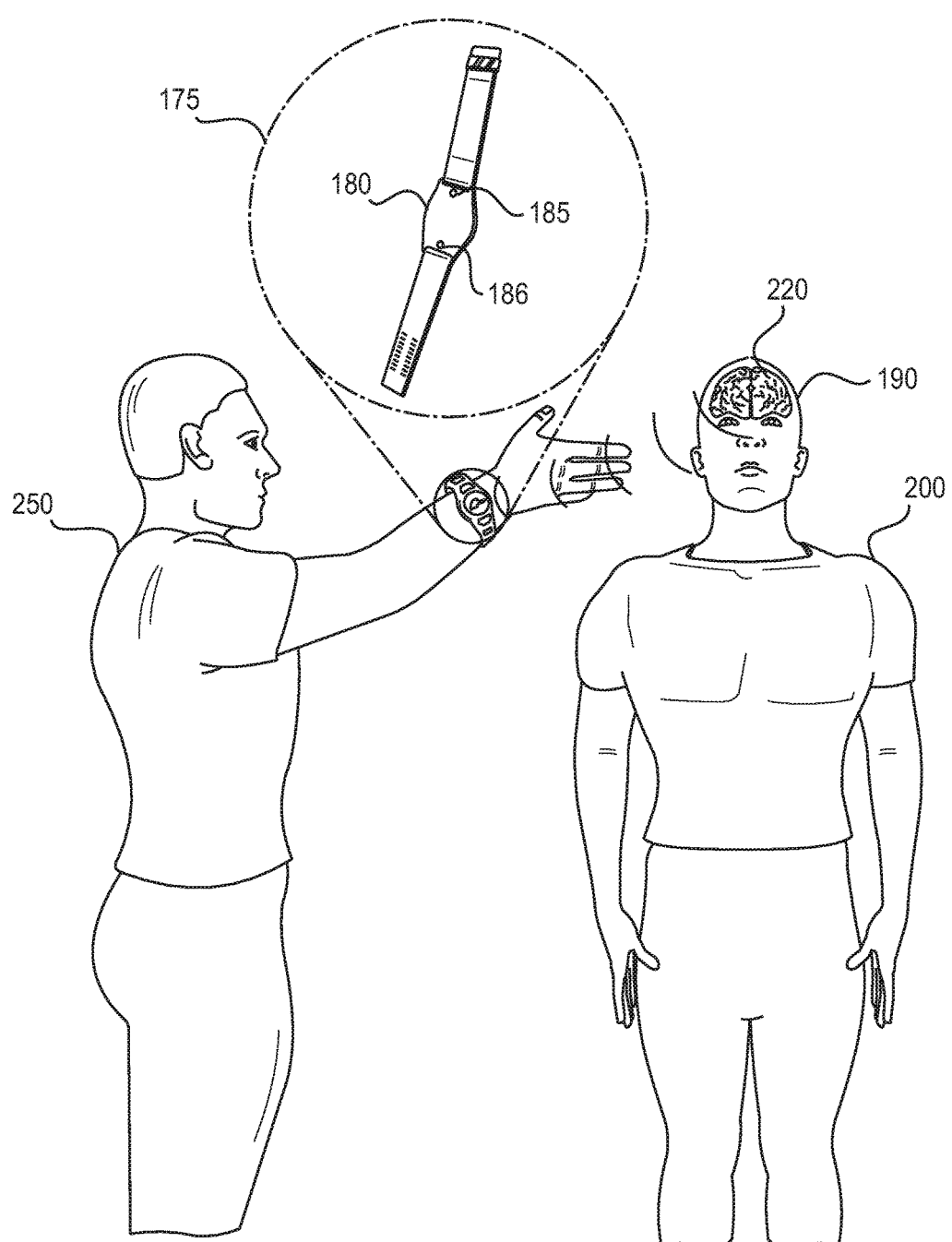
FIG. 7 illustrates an exemplary body-based amplifier with wireless transmitter unit and a non-body contact directional EEG device embedded in a single device, the non-body contact directional EEG device directed to the head of a second person to receive EEG signals from the head of a second person.

FIG. 7 illustrates an exemplary embodiment of a non-body contact/contact directional EEG device 175 shown as a wristband being worn by a first person 250 and directed toward the head of second person 200. The non-body contact directional EEG device 175 of FIG. 7 is configured for directional aiming to a portion of the head 190 of the person 200 to actively acquire EEG from the brain 220 of the second person 200 in proximity without physical contact with the second person 200. The non-body contact directional EEG device 175 can provide structural support for the internal amplifier and wireless transmitter units 180. The device can take the form of, but is not limited to, a wristband housing 175 with external sensor array 185 and 186 electrically connected to the amplifier and wireless transmitter unit as described above with reference to FIG. 1.

Figure 8:
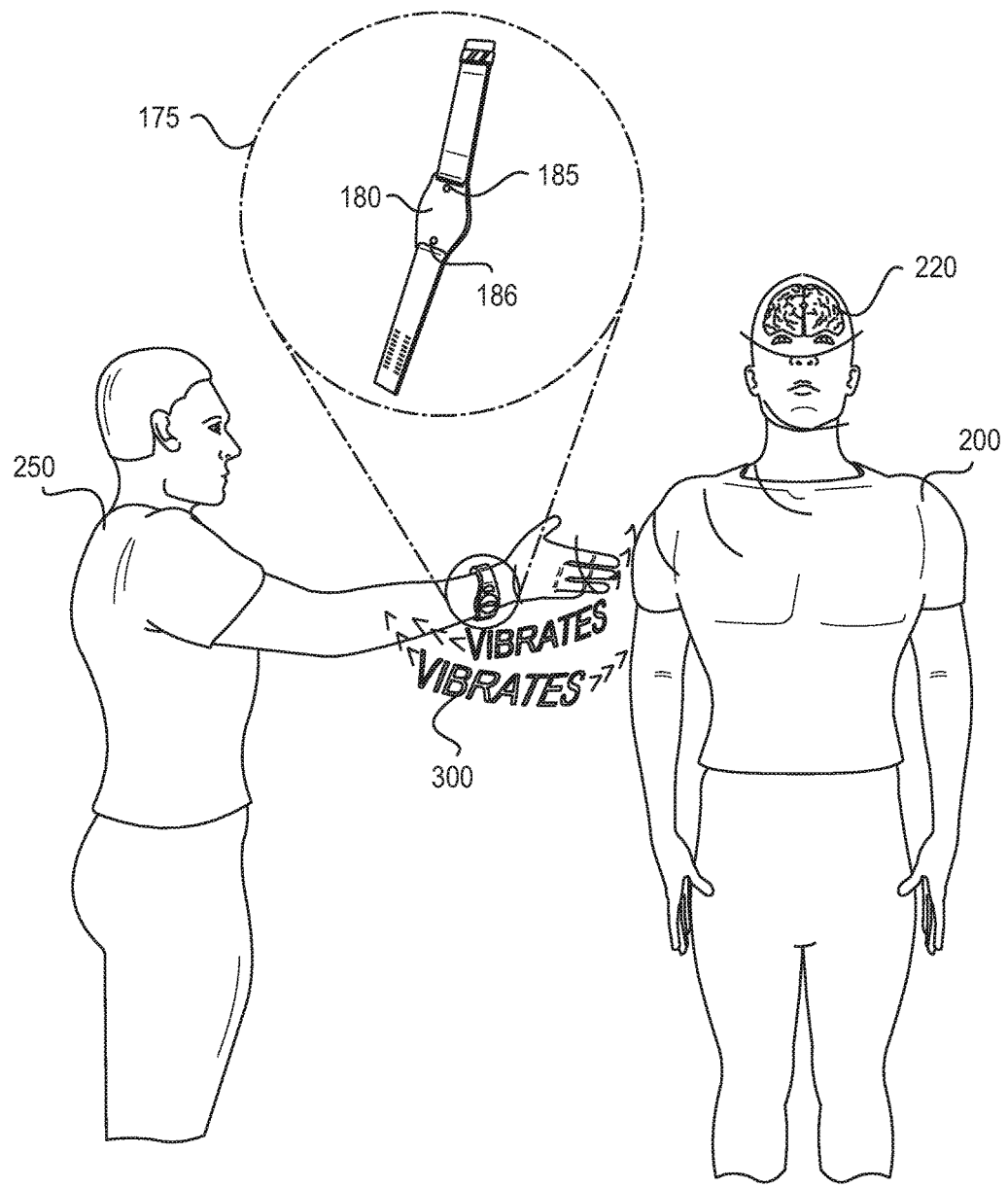
FIG. 8 illustrates an exemplary body-based amplifier with wireless transmitter unit and a non-body contact directional EEG device embedded in a single device, the non-body contact directional EEG device directed to the body of a second person to receive EEG signals from the body of a second person providing tactile/haptic response such as vibration to the body-based wearer.

FIG. 8 illustrates an exemplary embodiment of a non-body contact/contact directional EEG device 175 shown as a wristband worn by a first person 250 and being directed toward the body of a second person 200. The non-body contact directional EEG device 175 of FIG. 8 is configured for directional aiming to a portion of the body of the person 200 to actively acquire EEG from the brain 220 of a person 200 that is in proximity without physical contact with the second person 200. The non-body contact directional EEG device 175 provides structural support for the internal amplifier and wireless transmitter units 180, and more particularly takes the form of, but is not limited to, a wristband housing 175 with external sensor array 185 and 186 as described with reference to sensors 27 and 29 of FIG. 1 and is configured for directional aiming of the device to the body of a person 200. The resulting detected EEG data can be transferred to the shared Bluetooth radio and processed in the processor 40 as described above with reference to FIG. 1. The resulting signals can be used in algorithms to determine states, such as, but not limited to attention, stress, thought, peak performance, like/dislike, personal identity, other cognitive states, mental states, psycho-physiological states, and the like. The determined states can then be reported through a correlative tactile/haptic response such as, for example, selected vibrations opulses 300 to the body-based wearer 250.

The sensors 185 and 186 can be placed at least proximate to either a portion of the second person's 190 head, (FIG. 7) or the body 200 (FIG. 6) for non-contact EEG acquisition. Signal processing may then be employed to determine and drive a feedback device corresponding to the magnitude of brainwave activity in different brainwave frequency bands of interest to the first person 250 wearing the device 175.

The processor 40 and wireless receiver 36 or Bluetooth® device 36 of FIG. 1 can be employed in connection with the embodiment of FIGS. 6-8, and can similar function as described above with reference to FIG. 1. Of course, the processor 40 can be integrated into the device 175 so that it operates as a single unit without the need for wireless transmission.

Figure 9:
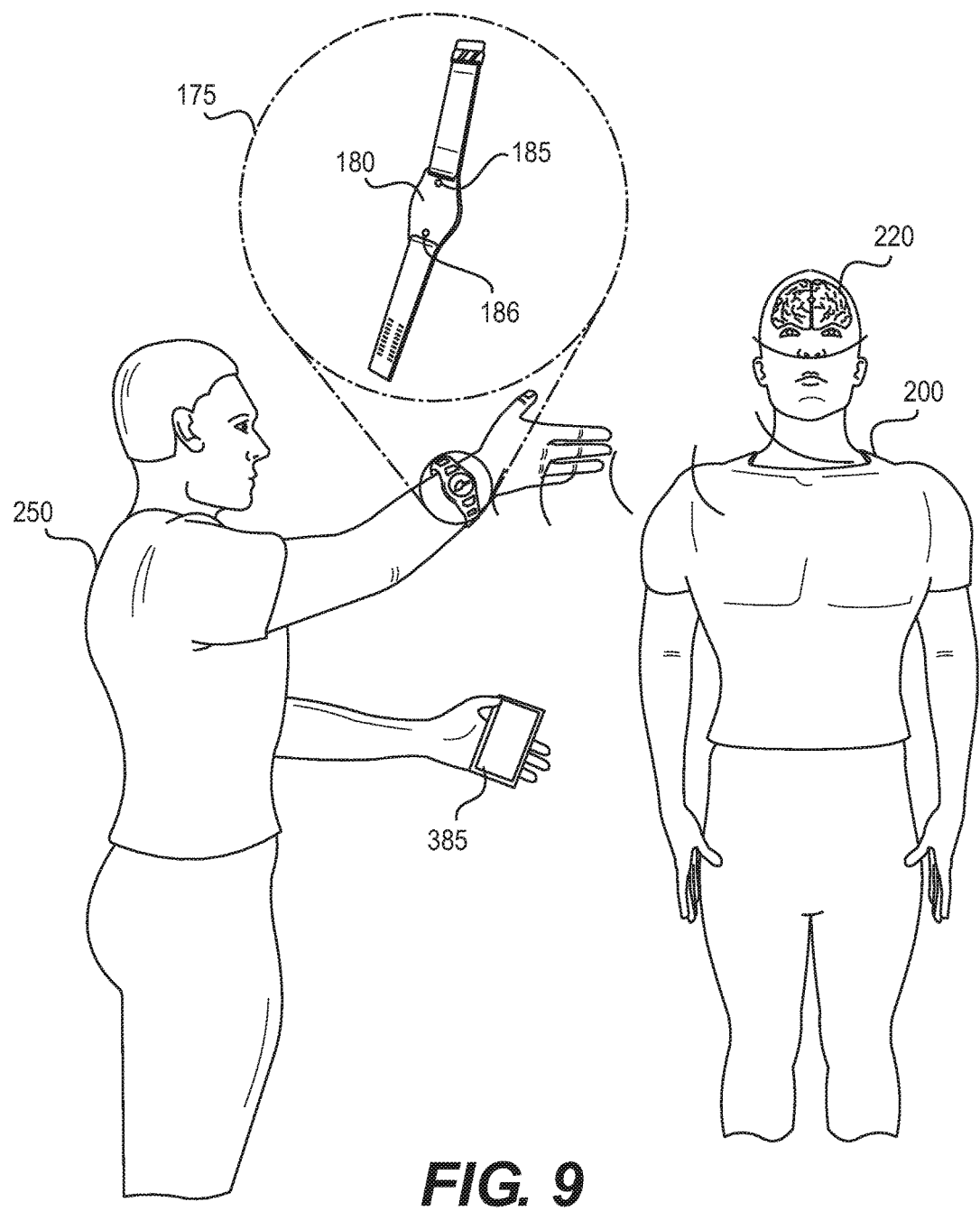
FIG. 9 illustrates an exemplary body-based amplifier with wireless transmitter unit and a non-body contact directional EEG device embedded in a single device, the non-body contact directional EEG device directed to either the body or head of a second person to receive EEG signals from the body of a second person and reporting second person's non-contact EEG data algorithmically changed to a cognitive or mental state which is then correlated to feedback on a cell phone.
Figure 10:
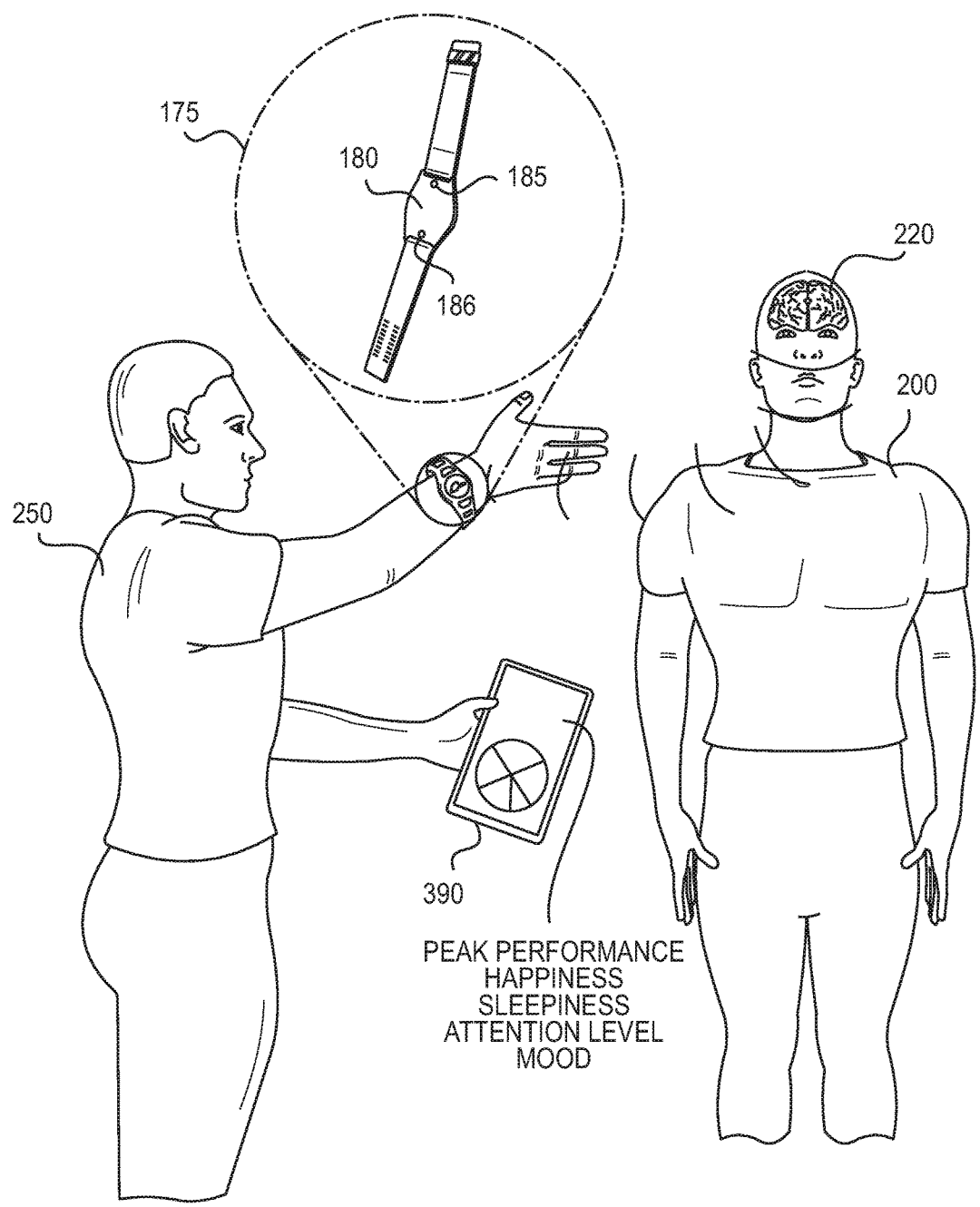
FIG. 10 illustrates an exemplary body-based amplifier with wireless transmitter unit and a non-body contact directional EEG device embedded in a single device, the non-body contact directional EEG device directed to either the body or head of a second person to receive EEG signals from the body of a second person and reporting the data on a tablet computer indicative of the cognitive or mental state of the non-contact EEG person.

FIGS. 9-10 illustrate exemplary embodiments of a non-body contact/contact directional EEG device 175 shown, for example, as a wristband worn by a first person 250 and being directed toward the body or head of a second person 200. The non-body contact directional EEG device 175 of FIG. 9 can be configured for directional aiming to a portion of the body or head of the second person 200 to actively acquire EEG from the brain 220 of the second person 200 in proximity without physical contact with that person 200. The non-body contact directional EEG device 175 can provide structural support for the internal amplifier and wireless transmitter units 180.

The device 175 can take the form of, but is not limited to, a wristband housing 175 with external sensor array 185 and 186 as described hereinabove with reference to sensors 27 and 29 of FIG. 1 and can be configured for directional aiming of the device to the body of the second person 200. The resulting EEG data may be transferred to the shared Bluetooth radio 32 and processed in the processor 40 as described above with reference to FIG. 1. Thus, the resulting EEG data can be further processed, for example, by a cell phone 385 or the like. Alternatively, the resulting EEG data can be processed entirely within the EEG device 175. The resulting signals can be used in algorithms to determine states, such as, but not limited to attention, stress, thought, peak performance, like/dislike, personal identification other cognitive states, mental states, psycho-physiological states, and the like, and provide feedback to a feedback device, such as a cell phone by, for example, correlatively changing a color on a ceil phone screen 385 to discreetly indicate the second person's 200 state as in FIG. 9.

Accordingly, as illustrated in FIG. 10, the resulting signals as described in FIG. 9 may also be reported by other feedback devices, such as a tablet computer 390, in a graphic format as illustrated in FIG. 10. This, may require a power supply to the dual EEG non-contact/contact wireless transmitter unit 175 which includes internal components, including battery (not shown), as described above with reference to the non-contact EEG directional circuit 25 of FIG. 1.

Figure 11:
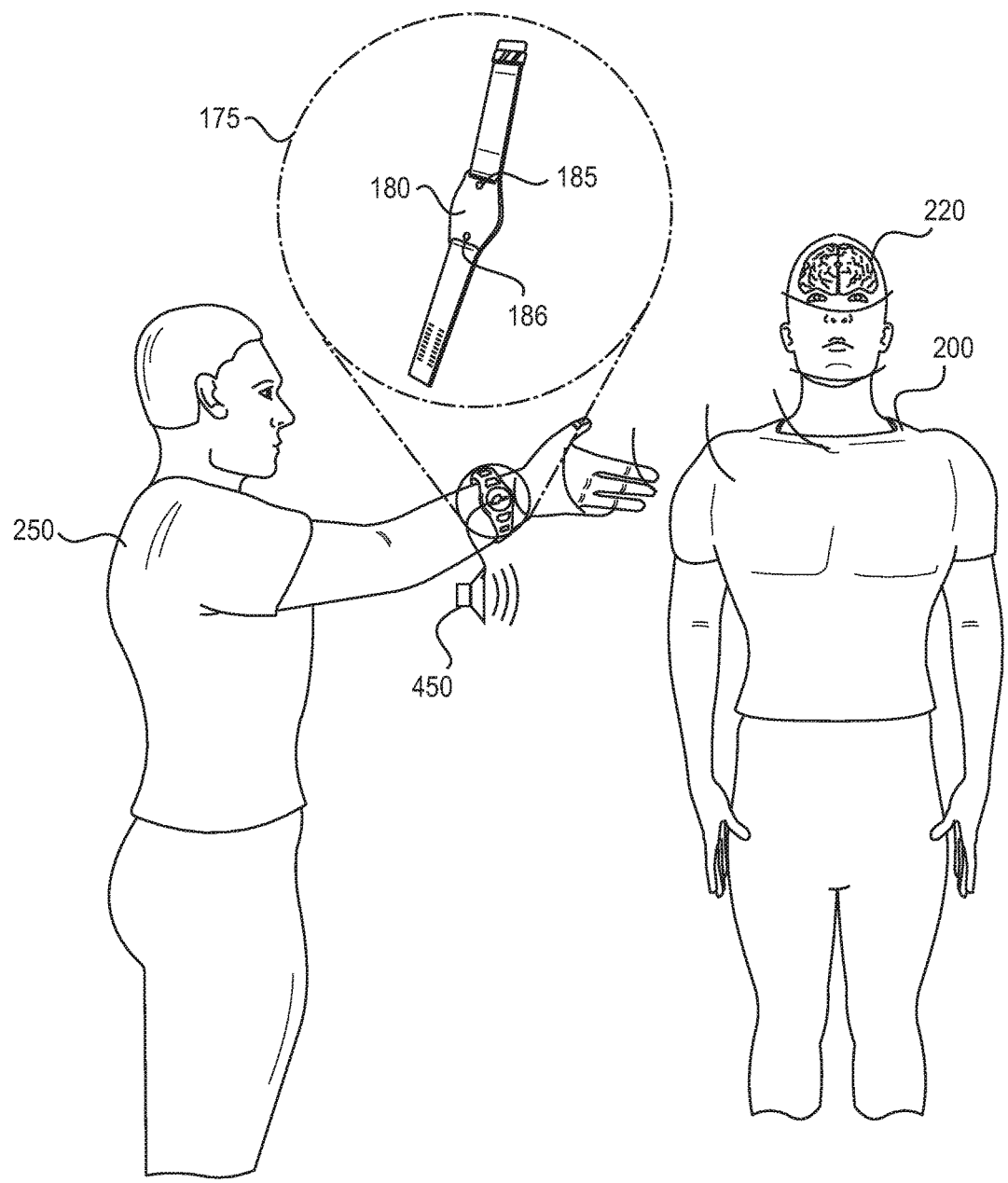
FIG. 11 illustrates an exemplary body-based amplifier with wireless transmitter unit and a non-body contact directional EEG device embedded in a single device, the non-body contact directional EEG device directed to the body of a second person to receive EEG signals from the body of a second person causing the auditory indication on the body worn device and/or a tablet computer to indicate the cognitive or mental state of the non-contact EEG person.

Two persons 250 and 200 respectively are represented in FIG. 11. The non-body contact/contact directional EEG device 175 is shown as a wristband being worn by first person 250 and is directed toward either the body or head of a second person 200. The non-body contact directional EEG device 175 of FIG. 11 is configured for directional aiming to a portion of the body or head of the second person 200 to actively acquire EEG signals from the brain 220 of the second person 200 in proximity and without physical contact with that person. The non-body contact directional EEG device 175 can provide structural support for the dual internal amplifier and wireless transmitter units 180, and more particularly takes the form of, but is not limited to, a wristband housing 175 with external sensor array 185 and 186 as described above with reference to sensors 27 and 29 of FIG. 1.

The resulting EEG data can be transmitted to the shared Bluetooth radio 32 and processed in the processor 40 as described herein above with reference to FIG. 1. Again, the resulting EEG data may be partially or entirely processed within the EEG device 175. The resulting signals can be used in algorithms to determine states, such as, but not limited to attention, stress, thought, peak performance, like/dislike, other cognitive states, mental states, psycho-physiological states, and the like, and thus provide an auditory feedback 450 to the person 250 wearing the device to indicate the other person's 200 state.

The sensors of FIG. 6-11, including the sensor 185 and 186 thus, during use in the dual non-body contact directional EEG device, can be positioned at least proximate to a portion of the person's 200 body below the head, and/or at the head 220 of another person 200.

Figure 12:
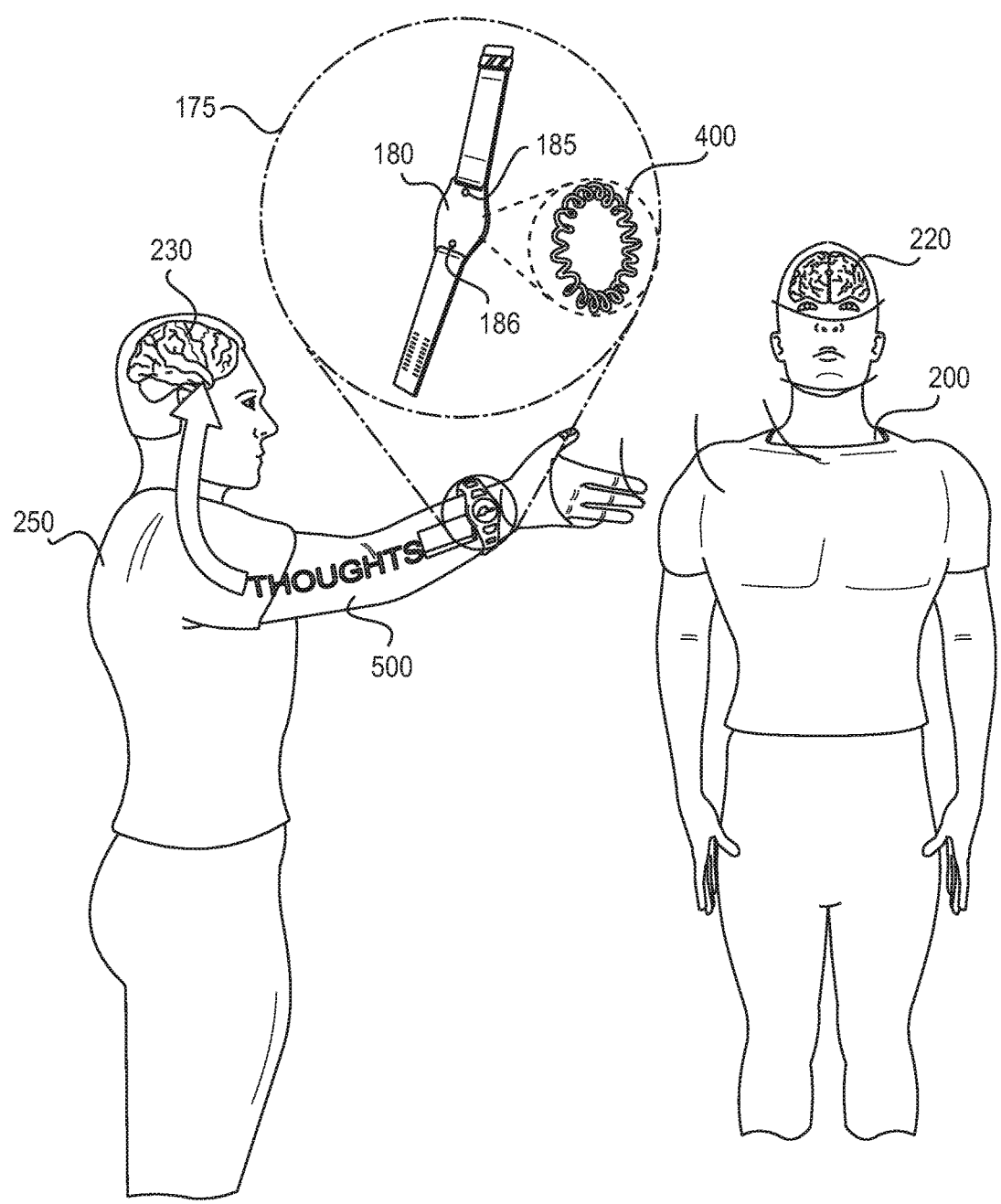
FIG. 12 illustrates an exemplary exemplary body-based amplifier with wireless transmitter unit and a non-body contact directional EEG device embedded in a single device the non-body contact directional EEG device directed to the body of a second person to receive EEG signals from the body of a second person, the single device decoding the EEG data, and transmitting those decoded signals as thoughts to the body-based wearer through the peripheral nervous system via single or multi-channel electro-magnetic sensor array, electro-magnetic coil or other transmission method.
Figure 13:
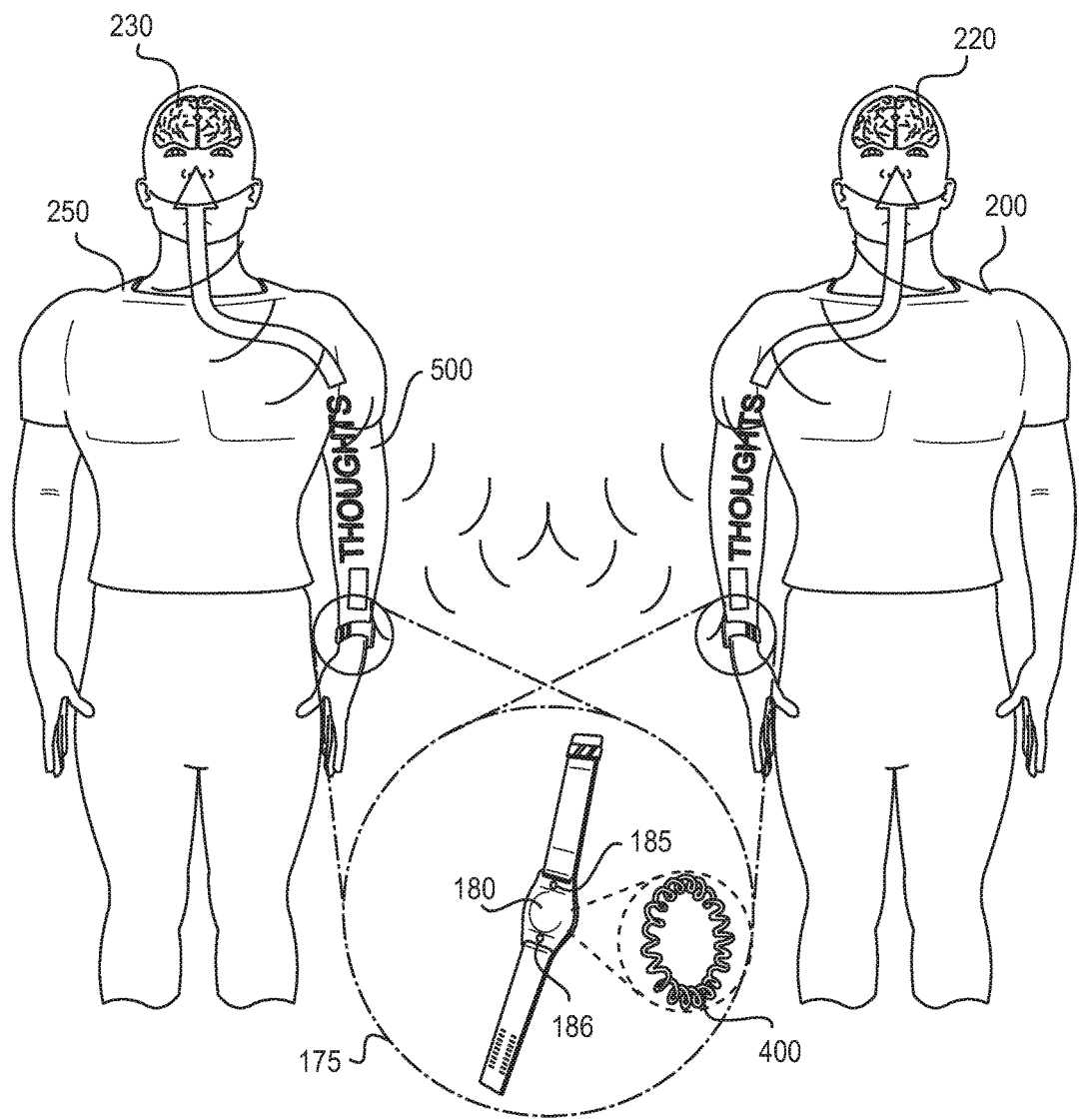
FIG. 13 illustrates an exemplary embodiment of the disclosure where two persons wear the non-body contact directional EEG device.
Figure 14:
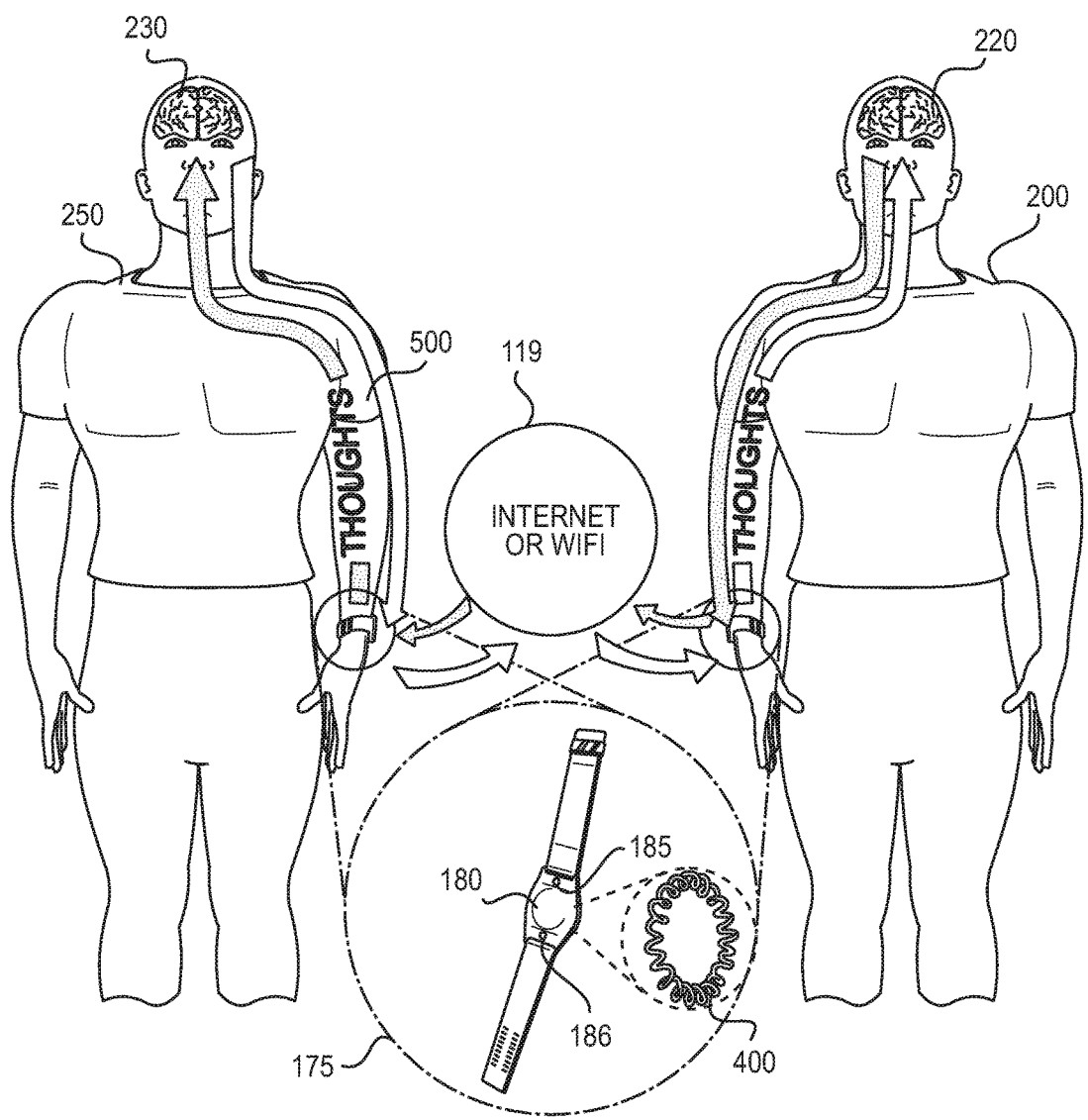
FIG. 14 illustrates another exemplary embodiment of the disclosure where two persons wear the non-body contact directional EEG device.

FIGS. 12-14 illustrate exemplary embodiments where all data collection, signal processing, and analysis functions can be performed in a single self-contained EEG non-contact/contact device 180 that can be worn by a first person 250 and placed proximate to either the body or head of a second person 200. The combination of two devices, body-based EEG acquisition and non-contact EEG acquisition embedded in a single wearable device, as referenced in FIG. 1, can transfer thought wirelessly and without vocalization from the brain of either one person to another, or between two separate persons. Such 'thought reader' technology can provide the basis for thought transfer over distance using personal wearable devices that acquire EEG waveforms through non-contact, then decode this information as thought or indication of a cognitive state such as stress or happiness on a digital signal processor using algorithm or transformations of the EEG data, and transmit those thoughts 500 to the brain 230 of a first person 250 wearing the device 175 via a feedback device. The feedback device can transfer thoughts 500 through, but not limited to, a multi-channel electro stimulator array (not shown) or electromagnetic sensor coil 400 connected to the peripheral nervous system. Such thought transfer 500 or 'mind reader' technology allows thoughts 500 to be shared without vocalization or physical connection to another human being.

Algorithms that indicate a cognitive state, such as stress, can be derived in many ways. For example, after all data are collected, down sampled, and filtered to remove various artifacts, a kernel density estimation (KDE) can be applied. In statistics, kernel density estimation (KDE) is a non-parametric way to estimate the probability density function of a random variable (e.g., EEG data among various individuals). Kernel density estimation is a fundamental data smoothing problem where inferences about a population are made (e.g., EEG stress indicators), based on a finite data sample which, in this instance, would be the EEG data collected from individuals or a subject population with the non-contact EEG device.

This could then be followed by applying a multilayer perceptron network ('MPN') to the data produced by the KDE. MPN using a back propagation algorithm are commonly used for learning pattern recognition processes in neuroscience. They are useful in algorithm development because one can derive approximate solutions for extremely complex problems like fitness approximation (determining stress data from the EEG population). An MPN is an artificial neural network (ANN). ANN are computing learning systems inspired by neural networks that constitute human brains. ANN learn similarly to a human brain which progressively improves performance on designated tasks by considering examples typically without necessitating task-specific programming. For example, in EEG stress recognition, an ANN would learn to identify trends in brain responses to stress by analyzing data that were produced when the human subject in the EEG subject group was submitted to stress and using the analytic results to identify stress indicators. An MPN can use data from a Power Spectral Density (PSD) rather than a KDE of the collected EEG data to learn what stress is among that population. It is important to note that the aforementioned processes and others unidentified here have been used in neuroscience to determine, e.g., stress from clinical EEG data produced from an EEG skull cap with a plurality of electrodes. However, this process has not been used to perform from a non-contact EEG device, as described in this disclosure.

It will be appreciated that aspects of this disclosure can be used to assign a neurometric, the science of measuring the underlying organization of the brain's electrical activity known as EEG. Certain brainwave frequencies are associated with general psychological processes. Neurometrics can be a method of quantitative EEG that provides a precise, reproducible estimate of the deviation of an individual record from normal.

Indeed, the aspects of the disclosure can use neurometrics to identify a person with an EEG output specifically their own as a personal identifier. Abnormal signal from this signature would be deemed false. This application of this can be coupled with other biometric marker technologies in the field to produce even stronger methods of identification.

FIG. 13 illustrates another embodiment of the disclosure where both a first person 250 and a second person 200 are wearing the non-body contact directional EEG device 175 with dual internal amplifier and wireless transmitter units 180. In this embodiment, the device 175 takes the form of, but is not limited to, a wristband housing 175 with external sensor array 185 and 186 that can be configured for directional aiming of the device to either the body or head of a person. Thus EEG data of the second person 200 can be detected by a non-contact EEG circuit 25, as described in FIG. 1, that is housed within the device 175 worn by the first person 250. In a similar manner, EEG data of the first person 250 can be detected by a non-contact EEG circuits that is housed within the device 175 worn by the second person 200.

The EEG data can be processed in the processor 40 of the respective devices 175 to decode the EEG data as thought on a digital signal processor as referenced in 495 of FIG. 4 using algorithmic transformations of the EEG data, and other data including, but not limited to heart rate, to reproduce thoughts 500 of person 200 and their brain 220 and transmit those thoughts 500 to the brain 230 of a person 250. Because both persons 200 and 250 are wearing the device 175, the first person 250 can now simultaneously transmit their EEG data in a similar matter to the embodiment described in FIG. 12 as thought to the second person 200, and vice versa, thus mentally conversing without vocalization.

In the embodiments described in this disclosure, the passing of thought occurs when a sender brain (person 1) emits a neural signal, e.g., "Hello" which has been interpreted through algorithmic function. In its most rudimentary form, the word, "Hello," may simply cause a peak at a specific EEG frequency of hertz or it can be specifically derived from algorithmic functions on various EEG bandwidths and/or frequencies. This is an analog signal that must be digitized via an analog to digital (A/D) converter which sends the digitized information to via Bluetooth, WiFi, or Internet to a separate person (person 2) wearing the invention as a receiver. The receiver device then uses DSP to re-encode the digitized information as a neural message that is then injected into person 2's peripheral nervous system by methods of, but not limited to, transcranial magnetic stimulation of the visual areas in the occipital cortex indirectly modulating neural activity through rapidly changing magnetic fields, electrically via an array of sensors proximate to the skin, or haptically stimulating the nerves that induce neural activity that can interpret the signal as, "Hello." These methods can also be used in combination as neurostimulation methods to exchange information between brains directly in neural code.

Further, it is highly foreseeable that improvements to other technologies will better permit the inducement of neural activity for communication between brains. For example, improvements in conductive materials, such as conductive hypoallergenic plastics, metals, and ceramics will greatly increase the ability to input data into the central and peripheral nervous systems of a wearer on the device. Additionally, cranial or transdermal implants could also facilitate direct input into the brain from the device. Future improvements can also include smaller and faster electronics technology, including higher fidelity versions of this device which will incorporate better analog to digital processors, multiple channels, more powerful processors, gyros, accelerometers, and the like.

FIG. 14 illustrates a similar embodiment as FIG. 13, with the exception that thought data 500 can be transferred to another person wearing the device 175 over greater distances using, but not limited to Wi-Fi, the Internet 119, a network, and the like.

Signal acquisition for monitoring electrical activity within the brain has been conventionally limited to the use of electrodes attached to the human head, and typically to the scalp, for a variety of reasons. EEG signal acquisition has been limited to electrodes attached to the head because EEG signals can be miniscule with poor spatial resolution. Past EEG devices are particularly sensitive only to post-synaptic potentials generated in superficial layers of the cortex. EEG signals are actually the result of millions of electrochemical pulses of energy fired across the synapse or minute divide between brain cells (neurons). The energy resulting from this process is very small and is measured in microvolts. Because the signal is incredibly minute, signal acquisition from anywhere other than the head has been considered to not be feasible.

Spatially, EEG sensors detect signals from the crests of gyri directly abutting the skull (the shortest distance between the two points) and radial to the skull. Energy produced from synapses located far deeper in the cortex, inside deep fissures (sulci), are in midline or deep structures, such as the hippocampus, or produce currents which are tangential to the skull only very nominally contribute to the EEG signal.

Further, EEG signal acquisition can be limited to electrodes attached to the head because the meninges (collective term for the three membranes covering the brain and spinal cord), cerebrospinal fluid, skull, and oils in the skin tend to obstruct and diffuse the EEG signal, obscuring its intracranial source. Conductive gels or special dry sensors conventionally are used to obtain EEG signals and overcome natural impedance, but such conductive gels or special dry sensors cannot eliminate the interference or obstruction caused by the meninges, cerebrospinal fluid, and skull.

Additionally, EEG signal acquisition can be limited to electrodes attached to the head because it can be mathematically impossible to reconstruct unique intracranial current source for a given EEG signal, because some currents produce potentials that cancel each other out. This is referred to as the inverse problem. As a result, as current and conventional practice, EEG signals are acquired or taken only from the head, either on the scalp itself, or via electrodes attached to the ears. Employing radio signal reception as a loose analogy or example, as one moves away from a radio transmitting antenna or a tower and towards the country, the signal not only weakens, but many more interfering factors arise like competing radio signals from neighboring stations, industrial noise, and physical obstructions.

In the present disclosure, sensors attached to portions of the body below the head develop raw signals which, when amplified and filtered as described hereinabove, provide useful analysis signals for monitoring electrical activity within the brain. Particularly useful and effective are embodiments wherein raw signals from the electrodes or sensors are filtered and analyzed to determine the magnitude of brainwave activity within particular frequency bands of interest which are indicative of level of attention. Stated in other words, it has been discovered that attentional brainwave monitors which include electrodes intended to be attached to the head can also effective when the electrodes (or other sensors such as non-contact bio-sensors) are attached/or example, to the arms.

Referring again to the embodiment shown in FIG. 14, a first person 250 wearing the device 175 is able to transmit thought to a second person 200 wearing a similar device 175. In operation, the device 175 worn by the first person 250 can detect EEG data from the brain 230 of the first person 250 via a contact EEG circuit 24, as described in FIG. 1, that is contained within the device 175. Similarly, the device 175 worn by the second person 200 can detect EEG data from the brain 220 of the second person 200 via a contact EEG circuit 24 that is contained within the device 175 worn by the second person 200. Processed EEG data can be transmitted between the first and second persons' devices 175. Transmission can take place via any means or combination of means, such as RF, BlueTooth, Internet, WiFi, or the like.

Similar to above, a receiver within the respective devices can use DSP to re-encode the digitized information as a neural message that can then be injected into a wearer's peripheral nervous system by methods of, but not limited to, transcranial magnetic stimulation of the visual areas in the occipital cortex indirectly modulating neural activity through rapidly changing magnetic fields, electrically via an array of sensors proximate to the skin, or haptically stimulating the nerves that induce neural activity that can interpret the thought of the other person.

Aspects of the disclosure can provide superior unique features relative to thought transfer. First, it can a wearable device that acquires EEG data wirelessly through non-contact with a separate human being, while simultaneously acquiring separate EEG data emanating from the wearer. Secondly, it can processes the acquired EEG from the non-contact acquisition party (person) and transmits those data as thought or simple cognitive state, mental state, or psych-physiological state. Thirdly, if two persons wear the device, it can acquire EEG signal using the dual non-contact and contact units, then processes data from each person and decodes it into thoughts and transmits those thoughts to the opposite wearer thus facilitating cross though transfer and thus communication without vocalization. Lastly, the device can be used to identify person without need for physical contact with the person. Identification can be made by the device being pointed at the person and comparing the person standing before you with their known EEG signature. A good example is to meet with a blind date and know this is the person communicating with you on the web via their personal EEG signature similar to their fingerprint. This would be known as a 'brainprint.' For example, a database of previously stored brain prints of numerous people can be searched to identify or confirm the identity of the person.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. A device for detecting electroencephalography (EEG) signals of a first person in proximity to the device, the device comprising:
a non-contact EEG directional circuit having non-contact sensors worn by a second person, the non-contact EEG directional circuit being configured to detect the EEG signals produced by a brain of the first person without making contact with the first person as the non-contact sensors worn by the second person are directed toward to a portion of the first person's body by a movement of the second person;
a processor coupled to the non-contact EEG directional circuit that is configured to analyze the EEG signals to detect patterns in the EEG signals that correspond to a state of the first person in proximity to the non-contacting sensors; and
a feedback device that is configured to provide the second person with an indication of the state of the first person in proximity to the non-contacting sensors.

2. The device according to claim 1, further comprising:
a contact EEG circuit having sensors that are in contact with the second person and that is configured to detect second EEG signals produced by a brain of the second person, wherein the processor is coupled to the contact EEG circuit and is configured to analyze the second EEG signals to detect patterns in the second EEG signals that correspond to a state of second the person.

3. The device according to claim 2, further comprising:
a transceiver that is configured to transmit the state of second the person to another device and receive a signal corresponding to a state of another person from the other device.

4. The device according to claim 3, wherein the feedback device provides the second person with the indication of the state of the other person based on the signal received by the transceiver.

5. The device according to claim 1, wherein the feedback device is at least one of a multi-channel electro stimulator array and an electromagnetic sensor coil.

6. The device according to claim 1, wherein the state of the first person in proximity to the non-contacting sensors includes at least one of an emotional state, a cognitive load state, and an alertness state of the first person.

7. The device according to claim 1, wherein the state of the first person in proximity to the non-contacting sensors includes at least one of attention, stress, thought, peak performance, like/dislike, cognitive states, mental states, and psycho-physiological states.

8. The device according to claim 1, wherein the processor further matches the detected patterns in the EEG signals to an EEG signature corresponding to the first person in proximity to the non-contacting sensors in order to identify the first person.

9. The device according to claim 1, wherein the processor further searches a database of EEG signatures for an EEG signature corresponding to the detected EEG signals produced by the brain of the first person in order to identify the first person.

10. A method for detecting electroencephalography (EEG) signals of a first person in proximity to a device, the method comprising:
detecting, by the device having non-contact sensors worn by a second person, the EEG signals, produced by a brain of the first person without making contact with the first person as the non-contact sensors worn by the second person are directed toward to a portion of the first person's body by a movement of the second person;
analyzing the EEG signals to detect patterns in the EEG signals that correspond to a state of the first person in proximity to the non-contacting sensors; and
providing the second person with an indication of the state of the first person in proximity to the non-contacting sensors.

11. The method of claim 10, further comprising:
adaptively determining heart rate signals of the first person from raw signals of the first person; and
filtering the raw signals to produce analysis signals including frequency components relevant to brain electrical activity while attenuating unrelated frequency components based on the heart rate signals to actively cancel heart rate signal components from the raw signals.

12. A method for detecting electroencephalography (EEG) signals of a first person in proximity to a device, the method comprising:
detecting, by the device having non-contact sensors worn by a second person, the EEG signals, produced by a brain of the first person without making contact with the first person as the non-contact sensors worn by the second person are directed toward to a portion of the first person's body by a movement of the second person;
analyzing the EEG signals to detect patterns in the EEG signals that correspond to a state of the first person in proximity to the non-contacting sensors by filtering raw signals of the first person to produce analysis signals including frequency components relevant to brain electrical activity to produce at least one bandpass-filtered state-indicating signal representative of raw signal magnitude within a predetermined frequency range as an indication of the state of the first person; and
providing the second person with an indication of the state of the first person in proximity to the non-contacting sensors.

13. The method of claim 12, further comprising:
processing the raw signals to produce at least one bandpass-filtered attention-indicating signal representative of raw signal magnitude within a predetermined frequency range as an indication of the first person's level of attention.

14. The method of claim 13, wherein processing the raw signals comprises:
bandpass filtering the raw signals to produce bandpass-limited signals within the predetermined frequency range; and
analyzing the bandpass-limited signals to determine a magnitude as the bandpass-filtered state-indicating signal.

15. The method of claim 14, wherein bandpass filtering the raw signals includes applying a low pass filter ahead of a bandpass filter.

16. The method of claim 12, further comprising:
actively determining heart rate signals of the first person from the raw signals; and
employing the determined heart rate signals to actively attenuate heart rate signal components from the raw signals.

17. An apparatus for detecting signals of a first person in proximity to the apparatus, the apparatus comprising:
a plurality of non-contact sensors worn by a second person; and
circuitry coupled to the plurality of non-contact sensors, the circuitry configured to:
detect the signals produced by a brain of the first person without making contact with the first person as the non-contact sensors worn by the second person are directed toward to a portion of the first person's body by a movement of the second person,
analyze the signals to detect patterns in the signals that correspond to a state of the first person in proximity to the non-contacting sensors, and
provide the second person with an indication of the state of the first person in proximity to the non-contacting sensors.

18. The apparatus of claim 17, further comprising:
an adjustable band configured for attaching the apparatus to an arm, leg, or torso of the second person.

19. The apparatus of claim 17, further comprising:
a cuff configured for attaching the apparatus to an arm or leg of the second person.

20. The apparatus of claim 17, wherein the circuitry is further configured to produce at least one bandpass-filtered attention-indicating signal as an indication of the first person's level of attention.

21. The apparatus of claim 17, further comprising:
a wireless transmitter for receiving signals from the plurality of non-contact sensors and wirelessly transmitting at least a portion of the signals.

22. The apparatus of claim 17, wherein the circuitry implements a bandpass filter to isolate frequency components of the signals within a predetermined frequency range relevant to at least one of the first person's: level of attention, cognitive state, physiological state, emotions, psychophysiological state, mental peak performance state, meditation state, and drowsiness/sleep states.

23. The apparatus of claim 17, wherein the circuitry implements a bandpass filter to isolate frequency components of the signals within a predetermined frequency range relevant to the first person's thoughts.

24. The apparatus of claim 17, wherein the circuitry includes a bandpass filter that isolates frequency components of the signals within a predetermined frequency range relevant to the first person's thoughts decoded by a digital signal processor, and sends the decoded thought signals to an electromagnetic stimulator that transmits the thought signals to the second person's brain via an electrode array or magnetic coil.

25. The apparatus of claim 17, wherein the circuitry includes a bandpass filter that isolates frequency components of the signals within a predetermined frequency range relevant to the first person's thoughts decoded by a digital signal processor, and sends the decoded thought signals to an electromagnetic stimulator connected to an array controller that transmits the thought signals to the second person's brain via an electrode array or magnetic coil.

* * * * *